United States Patent [19]

Campbell et al.

[11] Patent Number: 4,469,146
[45] Date of Patent: Sep. 4, 1984

[54] APPARATUS AND PROCESS FOR PREPARING QUANTITATIVE CHEMICAL SOLUTIONS

[75] Inventors: Jeptha E. Campbell, Cincinnati; James E. Gilchrist, Terrace Park, both of Ohio

[73] Assignee: Spiral Systems, Inc., Cincinnati, Ohio

[21] Appl. No.: 347,467

[22] Filed: Feb. 10, 1982

[51] Int. Cl.$^3$ ............................................. G01G 19/28
[52] U.S. Cl. ......................................... 141/9; 141/83; 177/70; 364/502
[58] Field of Search ......................... 141/1, 9, 83, 100; 177/25, 70; 364/502; 422/67

[56] References Cited

U.S. PATENT DOCUMENTS

| | | | |
|---|---|---|---|
| 3,240,146 | 3/1966 | Schreuder et al. | 141/83 X |
| 3,493,062 | 2/1970 | Bale, Jr. et al. | 177/70 |
| 4,222,448 | 9/1980 | Sunkle et al. | 177/70 X |
| 4,345,628 | 8/1982 | Campbell et al. | 141/83 |
| 4,350,186 | 9/1982 | Schalkowsky et al. | 141/83 |

OTHER PUBLICATIONS

*Fundamentals of Analytical Chemistry*, Holt, Rinehart & Wilson, Skoog & West, p. 199, 1963.
*International Encyclopedia of Chemical Science*, Van Nostrand, p. 745, 1964.

*Primary Examiner*—Stephen Marcus
*Assistant Examiner*—Mark Thronson
*Attorney, Agent, or Firm*—Antonelli, Terry & Wands

[57] ABSTRACT

This invention is an apparatus for making solutions of chemicals of specified molarity, normality, molality or weight percentage corrected, as necessary, for water of hydration in the solute. By means of an input-output device using a programmed instruction format, the desired chemical, the type of solution wanted, its concentration, and its volume are specified. An electronic balance with TARE capability repeatedly produces an output signal of the weight W of solute plus any solvent within a container in which the solution is to be mixed less the weight of the container. Apparatus are provided for calculating and storing the weight TW which is the total weight of the solute plus solvent which will result in a solution of the type and concentration of solution specified for the amount of solute placed on the balance. If the total volume of solution of the desired type and concentration of solution is specified, apparatus are provided for determining the amount of solute required. Means are provided for controlling the flow of solvent between a source and the container for causing the flow of solvent into the container when TW−W is greater than zero and to stop the flow of solvent into the container when $TW-W=0$. Apparatus are provided to prevent overfilling the container.

22 Claims, 12 Drawing Figures

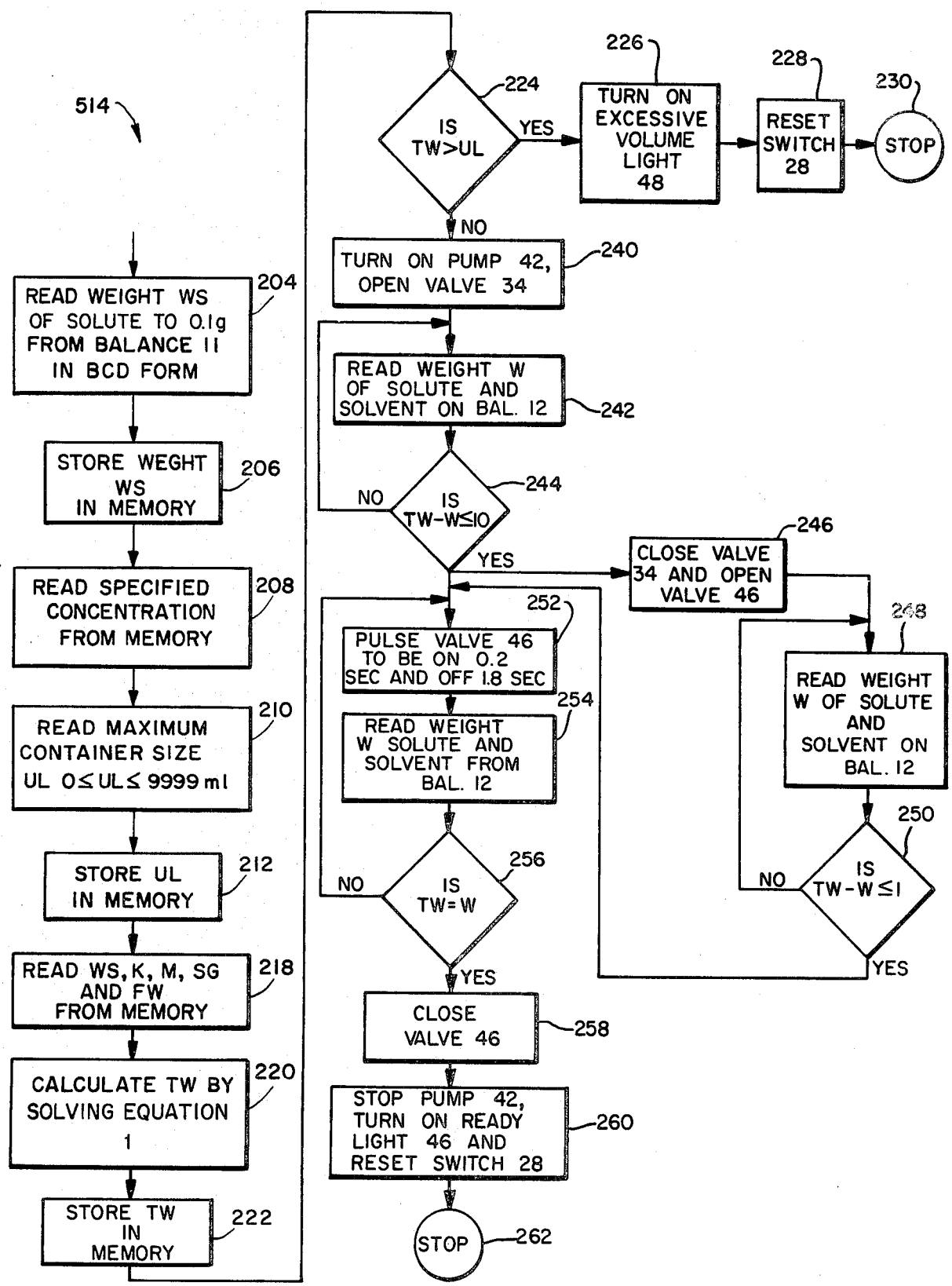
FIG. 4A. SUBROUTINE FOR MIXING MOLAR SOLUTIONS WITHOUT SPECIFIED VOLUME

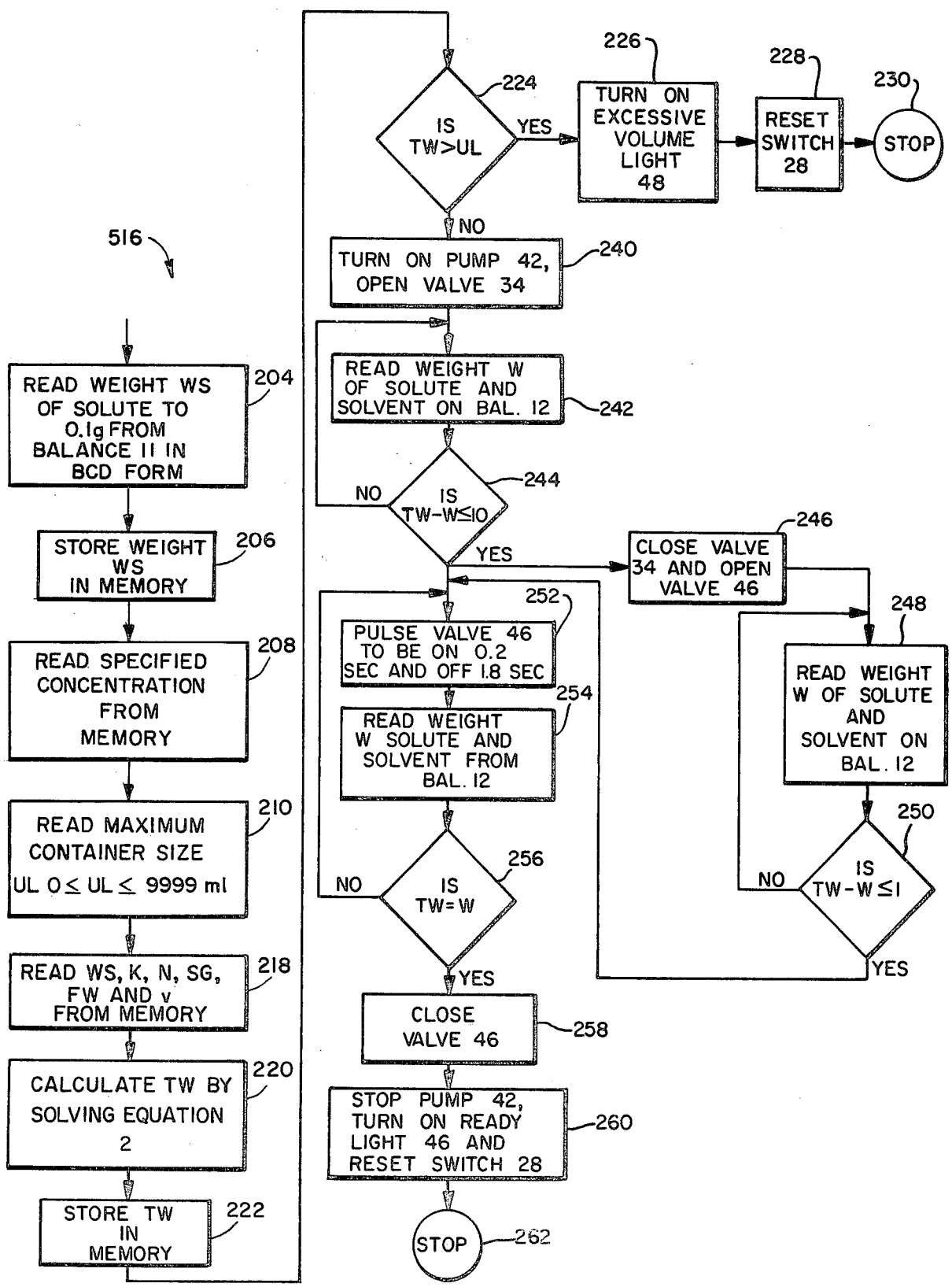
FIG. 4B. SUBROUTINE FOR MIXING NORMAL SOLUTIONS WITHOUT SPECIFIED VOLUME

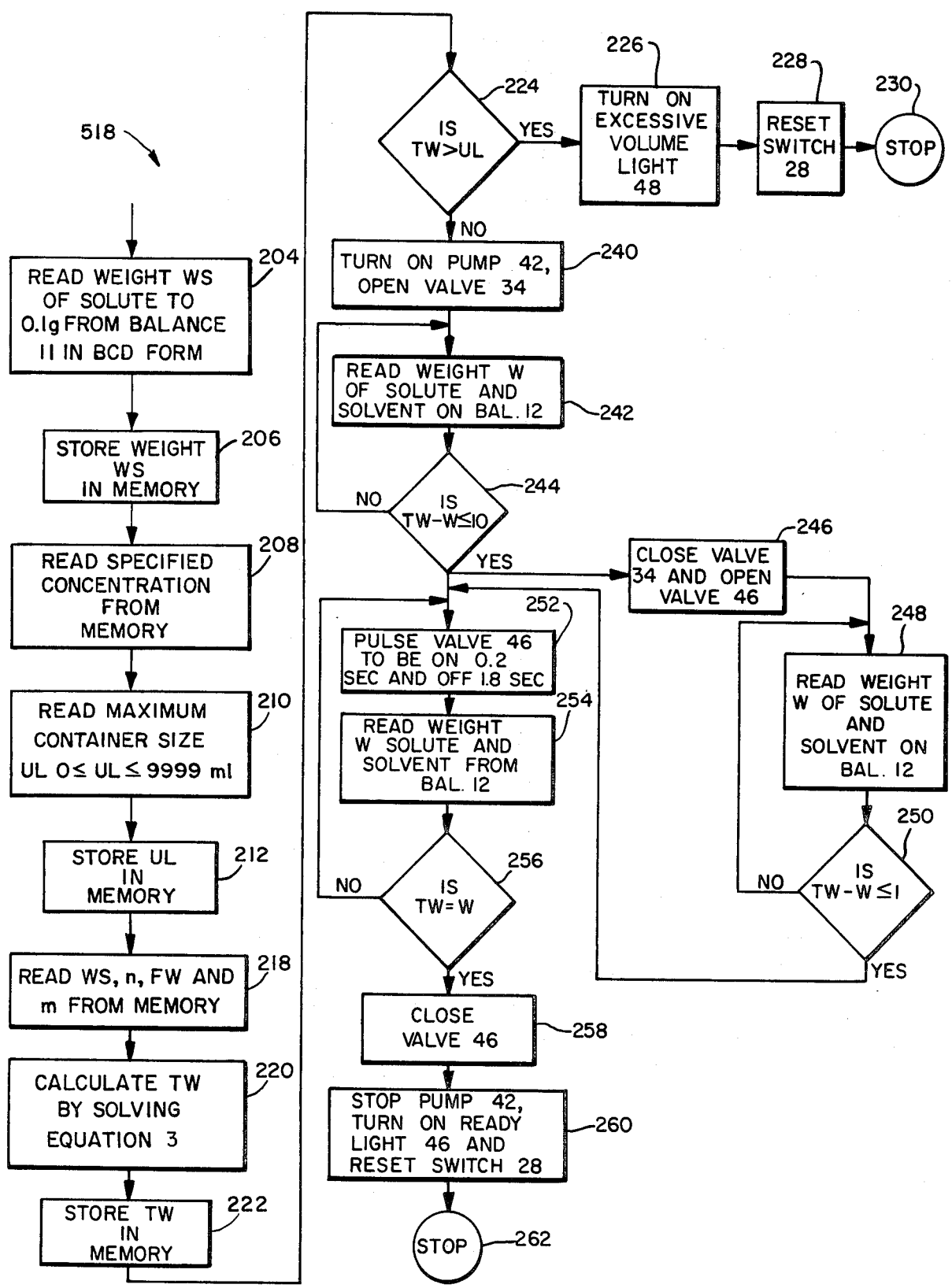
FIG. 4C. SUBROUTINE FOR MIXING MOLAL SOLUTIONS WITHOUT SPECIFIED VOLUME

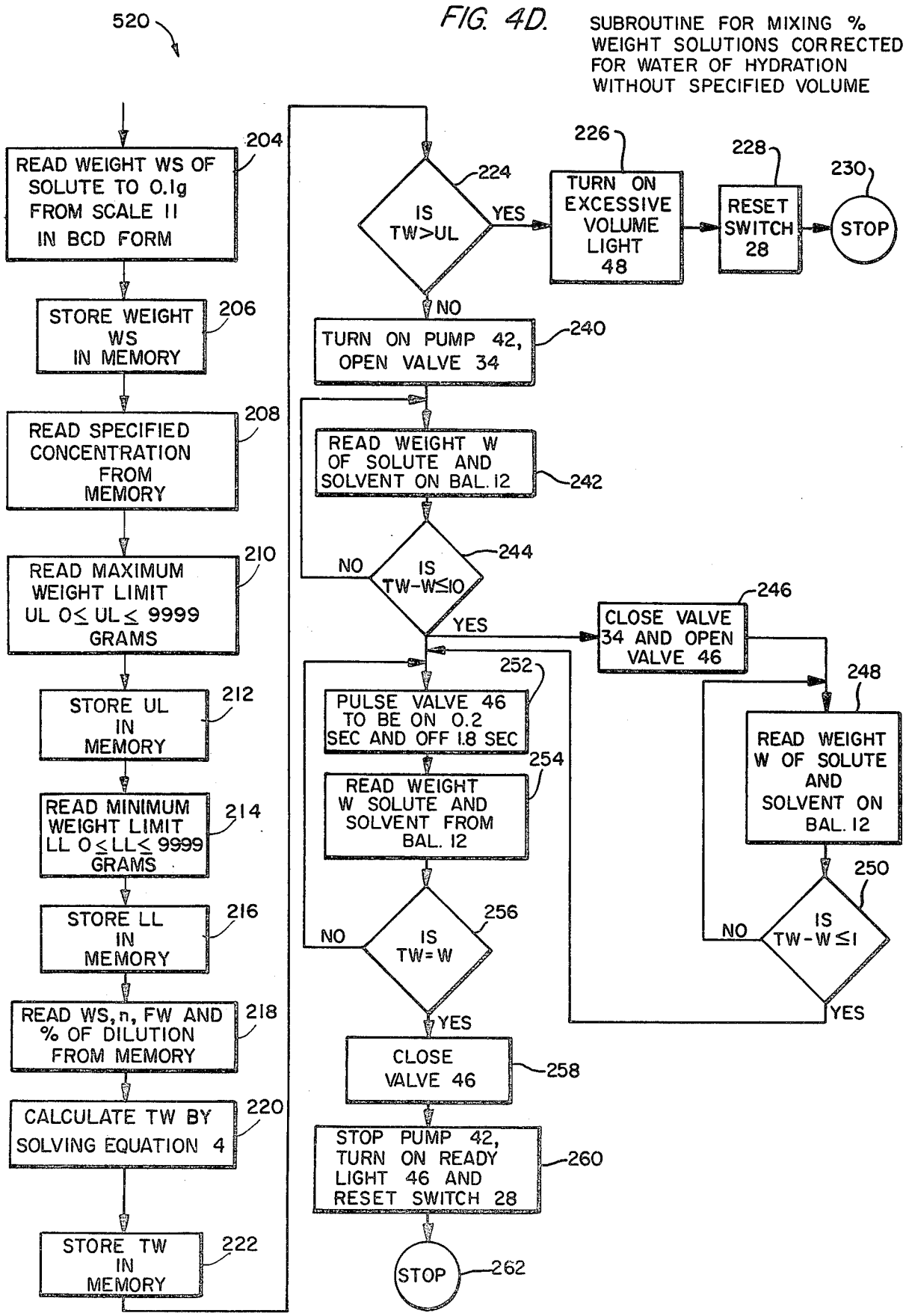

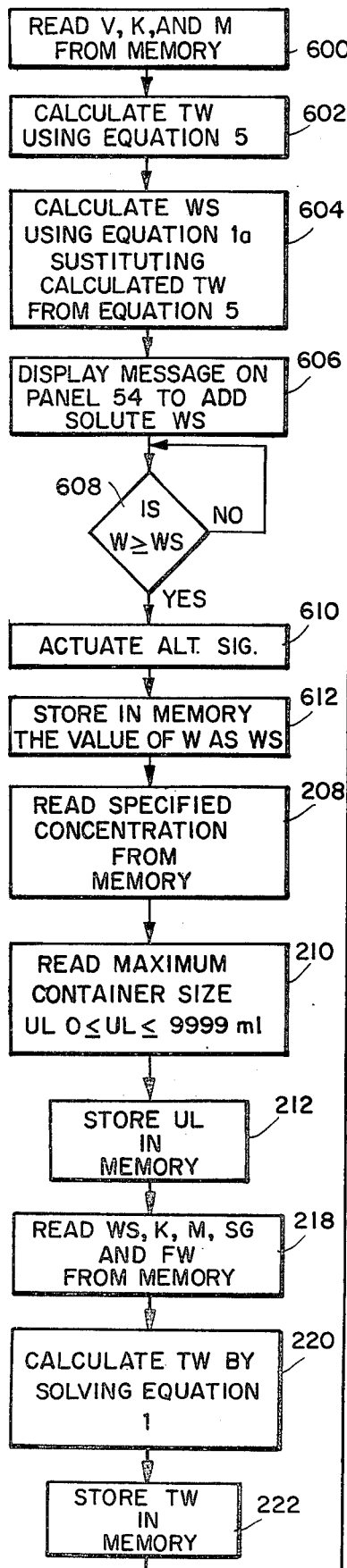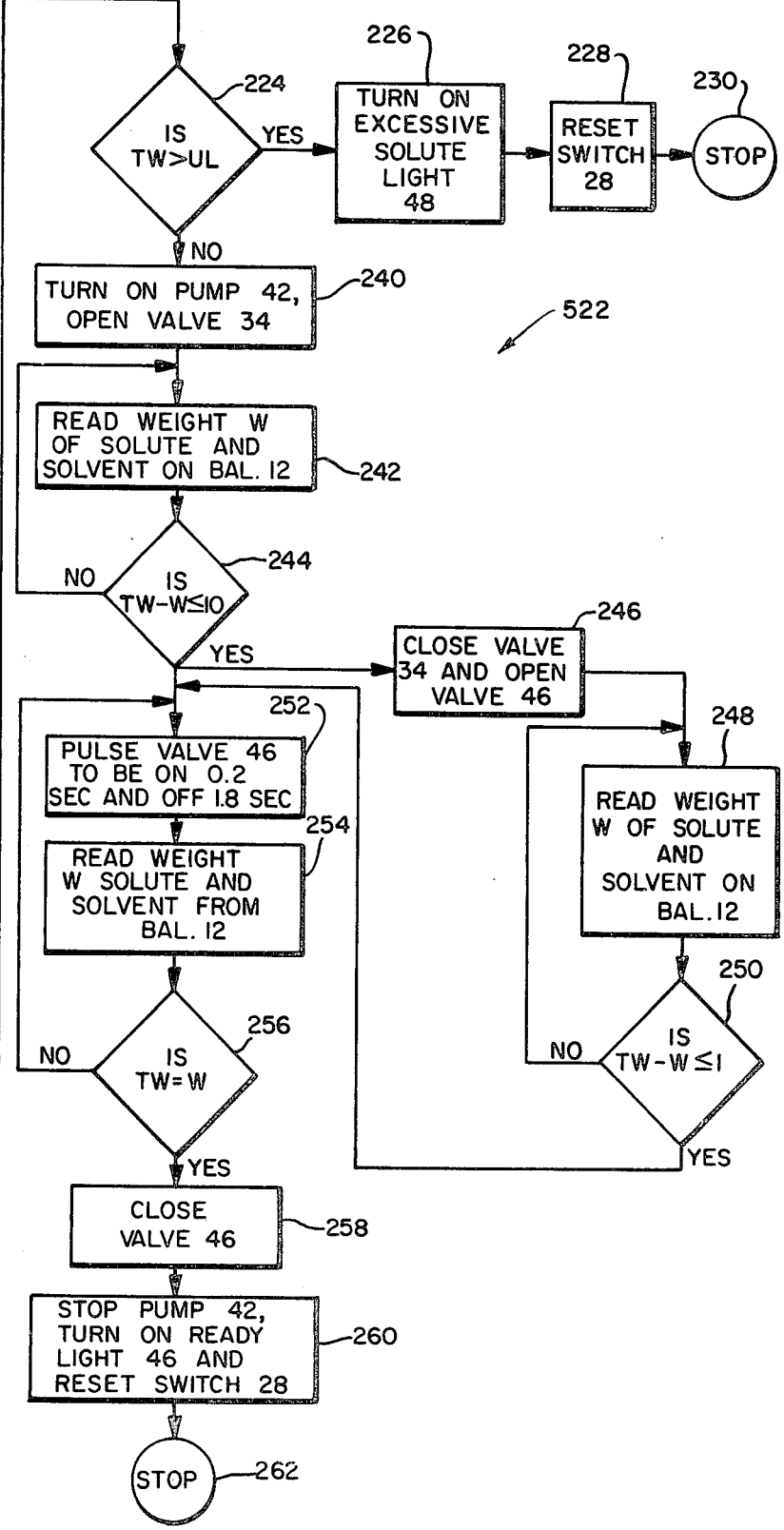
FIG. 4E.
SUBROUTINE FOR MIXING MOLAR SOLUTIONS OF SPECIFIED VOLUME

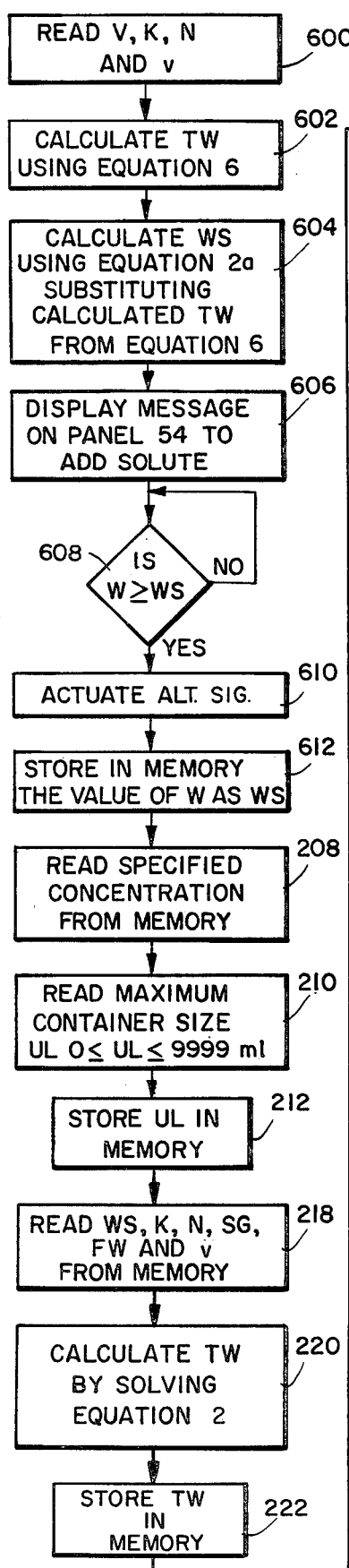
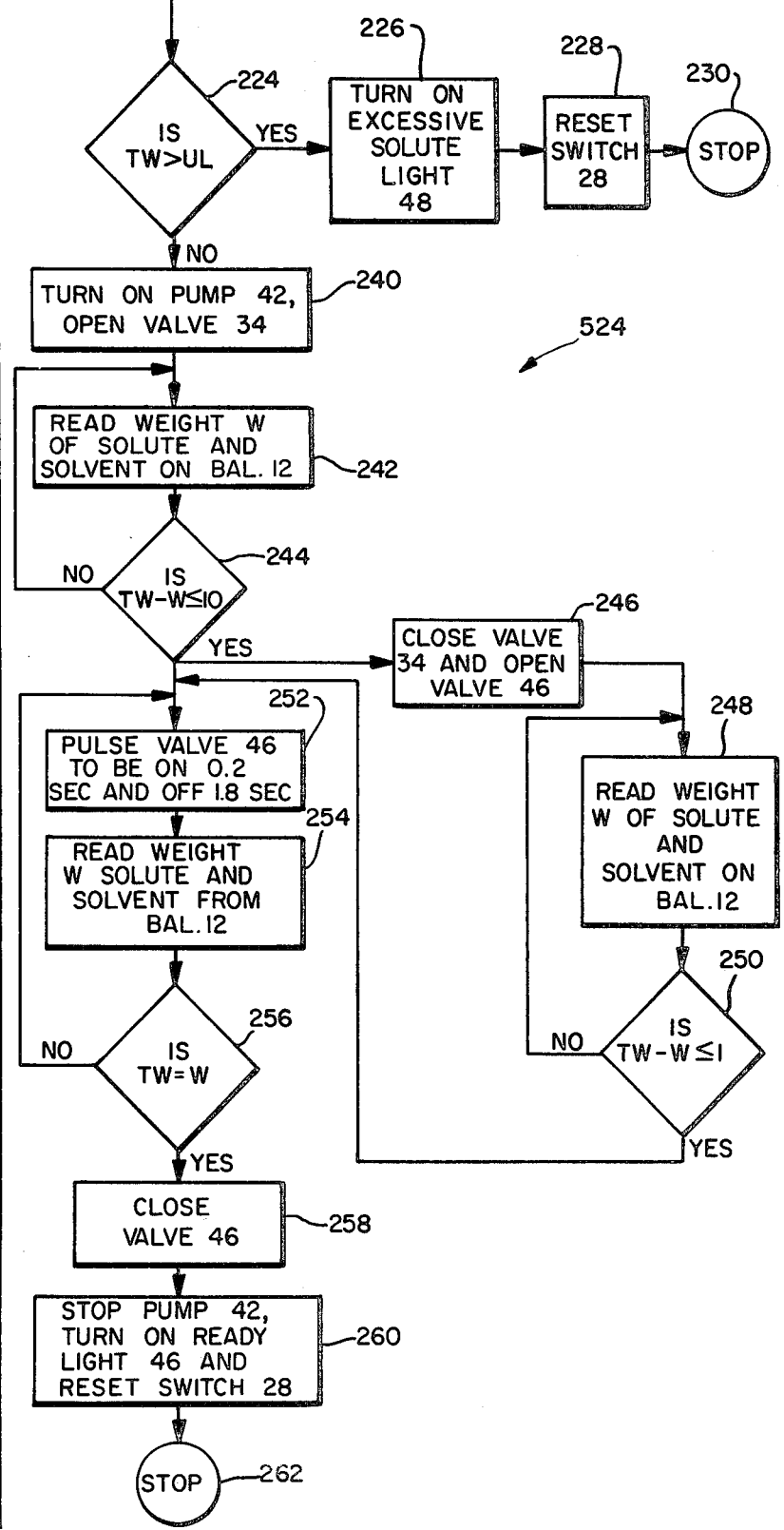
FIG. 4F.
SUBROUTINE FOR MIXING NORMAL SOLUTIONS OF SPECIFIED VOLUME

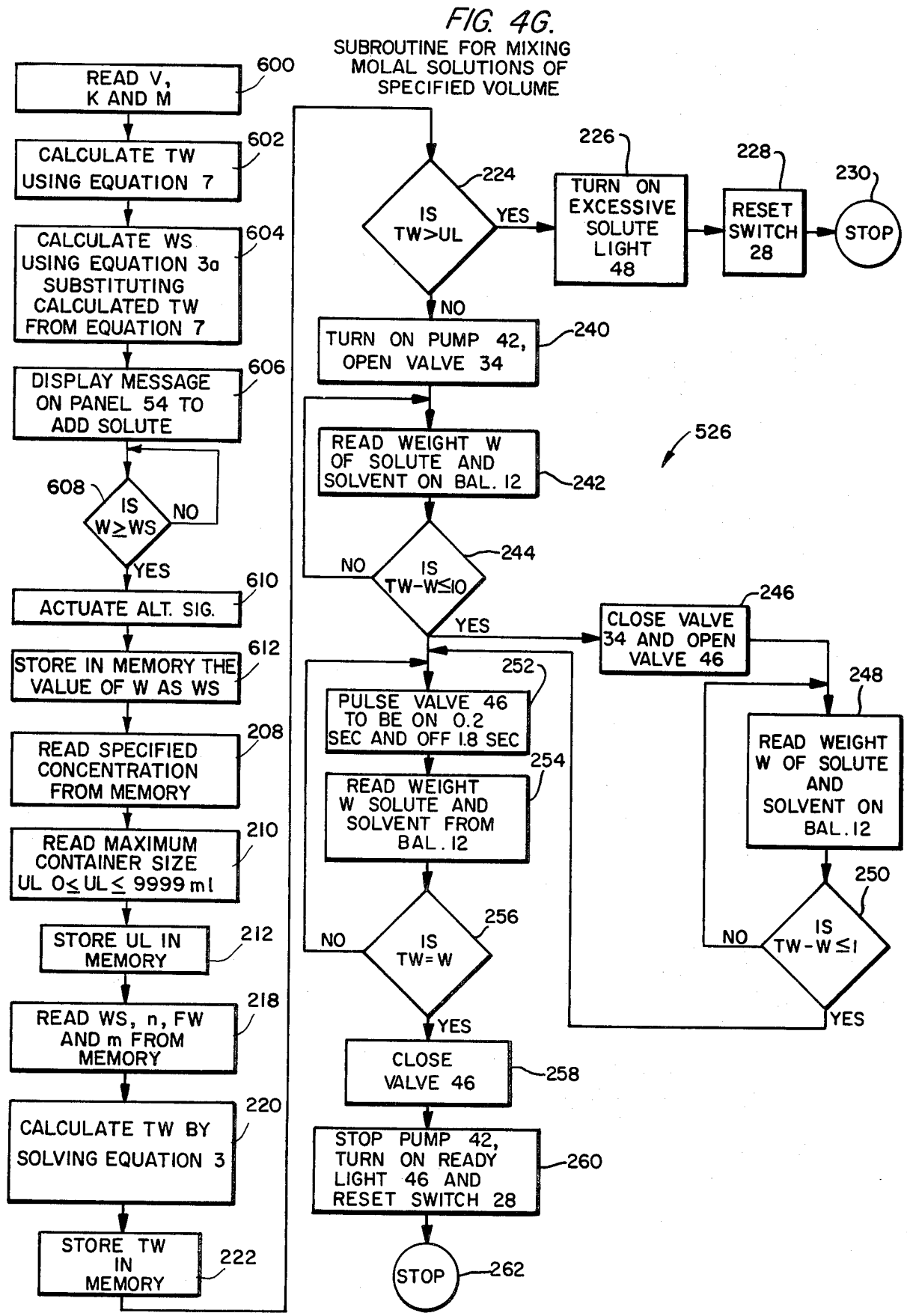
FIG. 4G. SUBROUTINE FOR MIXING MOLAL SOLUTIONS OF SPECIFIED VOLUME

SUBROUTINE FOR MIXING % OF WEIGHT SOLUTIONS CORRECTED FOR WATER OF HYDRATION OF SPECIFIED VOLUME

APPARATUS AND PROCESS FOR PREPARING QUANTITATIVE CHEMICAL SOLUTIONS

CROSS REFERENCES TO RELATED APPLICATIONS

Reference is made to application Ser. No. 232,525 which was filed on Feb. 9, 1981 now U.S. Pat. No. 4,345,628 which has the same inventors as the present invention and to application Ser. No. 232,531 which was also filed on Feb. 9, 1981 now U.S. Pat. No. 4,350,186, which names different inventors than the present application. These applications disclose apparatus for making weight percentage solutions which are not corrected for water of hydration.

BACKGROUND OF THE INVENTION

1. Field of the Invention

The invention relates to apparatus for making chemical solutions of specified molarity, normality, molality or weight percentage corrected for water of hydration in which the volume of the combined solution may be unknown or estimated.

2. Description of the Prior Art

In chemistry, chemical engineering, manufacturing, qualitative and quantitative analysis and other diverse fields, it is often necessary to make and use chemical solutions of predetermined molarity, normality, molality and weight percentage corrected for water of hydration. The definition of molar, normal and molal and weight percent composition solutions may be found in chemistry texts or handbooks.

Molar, normal and molal solutions are conventionally made by either mixing a standard solution of known higher concentration than the concentration which is wanted and diluting the solution with solvent to lower it to the desired concentration or mixing the required amount of solute and solvent directly to produce the desired concentration. In either method, the definition of the type of solution is employed to calculate the required amount of solute and solvent necessary to make desired concentration of solution; the appropriate amounts of solvent and solute are measured; and the desired solution is made by mixing the solvent and solute.

A weight percentage solution is conventionally made by calculating the weight of solute and solvent necessary to achieve the desired ratio of solute to solute plus solvent in accordance with the definition of a weight percentage solution. Weight percentage solutions should be corrected for water of hydration of the solute in accordance with known methods.

The making of solutions of the foregoing types in specified concentrations is time consuming and expensive especially where it is necessary to mix a large number of solutions using different solutes or a large number of solutions from the same solute of different concentration such as to perform a series of tests.

SUMMARY OF THE INVENTION

The present invention is an apparatus for making solutions of specified molarity, normality, molality, or weight percentage corrected for water of hydration in the solute where appropriate. These solutions are made by adding solvent to a solute which has been placed in a container on an electronic balance with TARE capability until the combined weight $W$ of the solvent plus solute $WS$ in the container is equal to a previously calculated weight $TW$ of solvent plus solute necessary to make the desired type of solution of specified concentration. The invention includes means for controlling the flow of solvent from a source to the container to cause the flow of solvent into the container from the source to continue until $TW=W$. The invention may make solutions of the foregoing types in which the volume of the solution is estimated or unknown.

Molar Solutions

The combined weight of solvent plus solute necessary to make a molar solution of a specified concentration may be expressed by the mathematical relationship $$TW = (1000)\left(\frac{WS}{FW \times M}\right)[[1 + (K \times M)](SG)] \quad (1)$$

where $TW$ is the combined weight of solvent plus solute necessary to make the desired molar solution, $K$ equals the specific gravity of a one molar solution of the solute at a specified temperature $-1$, which is stored in memory, $SG$ is a scaling factor which corrects for the variation in the specific gravity of a one molar solution as a function of temperature, $WS$ equals the weight of the solute to be mixed with the solvent to make the desired solution, $FW$ equals the gram molecular weight of the solute which is stored in memory and $M$ is the specified molarity. In accordance with the invention, the scaling factor $SG$ may be omitted from the equation for calculating $TW$ for molar solutions if $K$ is based on data measured at a temperature close to the actual temperature of mixing of the desired molar solution or if maximum accuracy is not required.

In accordance with the invention when the final volume of solution is not specified, the weight of the solute $WS$ placed in the container for making the molar solution is read and stored in memory, the calculation of $TW$ is made by solving the above identified equation (1) with the stored and operator specified values, the combined weight $W$ of solvent plus solute is repeatedly read out from the balance on which the container rests in which the solution is being made as solvent is added to the container, and the flow of solvent is continued until the combined weight of the solvent plus solute $W$ within the container equals $TW$.

If the volume $V$ of solution is specified, its gravimetric equivalent $TW$ is calculated by multiplying the volume $V$ by its specific gravity, as shown by the mathematical relationship $$TW=(V)[1+(K \times M)] \quad (5)$$

in which $TW$ is the combined weight of solvent plus solute necessary to make the desired molar solution, $V$ is the specified volume of the desired molar solution, $K$ equals the specific gravity of a one molar solution of the solute at a specified temperature $-1$ and $M$ is the desired molarity. After $TW$ is calculated in equation (5), it is used along with the other specified and stored values for solving equation (1) transposed for the solution of $WS$ as shown in the following equation $$WS = \frac{TW \times FW \times M}{1000[1 + (K \times M)]} \quad (1a)$$

When an amount of solute WS, which is equal to or greater than the value WS determined from equation (1a), has been placed on the balance, the operator is so alerted by audible and visual signals. The weight of solute WS, which has been placed on the balance to be used in making the molar solution is read and stored, the calculation of TW is made by solving the above identified equation (1), the combined weight W of solvent plus solute is repeatedly read out from the scale on which the container rests in which the solution is being made as solvent is added to the container, and the flow of solvent is continued until the combined weight of the solvent plus solute W within the container equals TW.

Normal Solutions

The combined weight of solvent plus solute necessary to make a normal solution of specified concentration may be expressed by the mathematical relationship $$TW = (1000)\left[\frac{WS}{\left(\frac{FW}{v}\right) \times N}\right]\left[\left[1 + \left(\frac{K}{v} \times N\right)\right](SG)\right] \quad (2)$$

where TW is the combined weight of solvent plus solute necessary to make desired normal solution, FW is the formula weight of the chemical compound stored in memory, K equals the specific gravity of a one molar solution of the solute at a specified temperature which is stored in memory $-1$, SG is a scaling factor which corrects for the variation in specific gravity of a one molar solution as a function of temperature, WS equals the measured weight of the solute that is to be mixed with the solvent to make the desired solution, N equals the specified normality which is entered into memory by the operator prior to mixing and v equals the valence of the chemical compound which is stored in memory. In accordance with the invention, the scaling factor SG may be omitted from the equation for calculating TW for normal solutions if K is based on data measured at a temperature close to the actual temperature of mixing of the desired normal solution or if maximum accuracy is not required.

In accordance with the invention when the final volume of solution is not specified, the weight of the solute WS placed in the container on the balance for making the solution is read and is stored in memory, the calculation of TW is made by solving equation (2) with the stored and specified values, the combined weight of solute plus solvent W is repeatedly read out from balance on which the container rests in which the solution is being made as solvent is added to the solute within the container, and the flow of solvent is continued until the combined weight of solute plus solvent W in the container equals the calculated weight TW.

If the volume V of solution is specified, its gravimetric equivalent TW, is calculated by multiplying the volume V by its specified gravity, as shown by the mathematical relationship $$TW = (V)\left[1 + \left(\frac{K}{v} \times N\right)\right] \quad (6)$$

in which TW is the combined weight of the solvent plus solute necessary to make the desired normal solution, V is the specified volume of the desired normal solution, K equals the specific gravity of a one molar solution of the solute at a specified temperature $-1$, v is the valence of the solute, and N is the desired normality. After TW is calculated using equation (6), it is used along with the other stored and specified values for solving WS from equation (2) transposed for the solution of WS as shown in equation (2a)

$$WS = \frac{(TW)\left(\frac{FW}{v}\right)(N)}{(1000)\left[1 + \left(\frac{K}{v} \times N\right)\right]} \quad (2a)$$

When the amount of solute WS which is equal to or greater than the value WS determined from equation (2a) has been placed on the balance, the operator is so alerted by an audible and visual signal. The final weight of solute WS along with the other stored and specified values are then used to solve the above identified equation (2) for TW. The combined weight of solvent plus solute W is repeatedly read out from a balance on which the container rests in which the solution is being made as solvent is added to the solute within the container, and the flow of solvent is continued until the combined weight of solute plus solvent within the container equals the calculated weight TW.

Molal Solutions

The combined weight of solvent plus solute necessary to make a molal solution of a specified concentration may be expressed in the mathematical relationship $$TW = \left[\frac{WS\frac{[1-18.02 \times n]}{FW}}{[FW-(18.02 \times n)] \times m}\right][[[FW-(18.02 \times n)] \times m] + 1000] \quad (3)$$

where TW equals the combined weight of solvent and solute necessary to made a molal solution of specified concentration, WS equals the gram molecular weight of the compound stored in memory, n equals the number of water molecules associated with each molecule of compound within its crystalline structure which is stored in memory and m equals the specified molality of the solution which has been entered into memory by the operator prior to mixing. The quantity 18.02 equals the molecular weight of water.

In accordance with the invention when the final amount of solution is not specified, the weight of the solute WS placed in the container on the balance for making the solution is read and stored in memory, the calculation of TW is made by solving equation (3), the combined weight of solute plus solvent W is repeatedly read out from the balance on which the container rests in which the solution is being made as solvent is added to the solute within the container, and the flow of solvent is continued until the combined weight of solute plus solvent W in the container equals the calculated weight TW.

If the volume V of the solution is specified, its gravimetric equation TW is calculated by multiplying the volume V by an estimate of its specific gravity. The following mathematical relationship may be used $$TW = (V)[1+(K\times M)] \quad (7)$$

where TW is the combined weight of solvent and solute, V is the desired volume, K is the specific gravity of a one molar solution of the solute at a specified temperature $-1$ and m is the desired molality. After TW is calculated in equation (7), TW is used along with the other specified and stored values to solve equation (3) transposed for the solution of WS as shown in equation (3a).

$$WS = \frac{(TW)[FW-(18.02\times n)](m)(FW)}{[[[FW-(18.02\times n)]\times m]+1000][FW-(18.02\times n)]} \quad (3a)$$

When the amount of solute WS which is equal to or greater than the value WS determined from equation (3a) has been placed on the balance, the operator is so alerted by audible and visual signals. The final weight of solute (WS) along with the other specified and stored values are used to solve equation (3) for TW. The combined weight of solvent plus solute W is repeatedly read out from the balance on which the container rests in which the solution is being made as solvent is added to the solute within the container, and the flow of solvent is continued until the combined weight of solute plus solvent within the container equals the calculated weight TW.

Weight Percentage Solutions Corrected For Water Of Hydration

The combined weight of the solvent plus solute TW necessary to make a weight percentage solution of specified concentration corrected for water of hydration may be expressed by the equation $$TW = \frac{(WS)\left[1 - \frac{(18.02\times n)}{FW}\right](100)}{\%} \quad (4)$$

where WS is the measured weight of solute that is to be mixed with the solvent to make the desired solution, FW equals the gram molecular weight of the compound stored in memory and n equals the number of molecules of water which are associated with each molecule of the solute in its crystallized state which is stored in memory and the % is the desired weight dilution factor.

In accordance with the invention, when the final amount of solution is not specified, the weight of the solute WS placed in the container for making the solution is read and stored in memory, the calculation of TW is made by solving the above identified equation (4). The combined weight of solvent plus solute W is repeatedly read out from the balance on which the container rests in which the solution is being made as the solvent is added to the solute within the container is contained until the combined weight of solute plus solvent W in the container equals the calculated weight TW.

If a final volume is specified, its gravimetric equivalent TW is estimated using the following mathematical relationship $$TW = V\left[1 + \frac{(K\times \%\times 10)}{FW - (18.02\times n)}\right] \quad (8)$$

where TW is the combined weight of solvent plus solute, V is the desired volume, % is the concentration desired, 18.02 is the molecular weight of water, n is the number of molecules of water combined in each molecule of the solute, FW is the gram molecular weight of the solute, and K equals the specific gravity of a one molar solution of the solute at a specified temperature $-1$. Using the TW estimated from the specified volume, along with other stored and specified values, WS is calculated by a substitution in equation (4) transformed for the solution of WS as shown in the following equation $$WS = \frac{(TW)(\%)(FW)}{(100)[FW - (18.02\times n)]} \quad (4a)$$

When this amount of solute WS has been placed in the container on the balance, the operator is alerted by visual and audible signals. The final weight of solute along with the other stored and specified values are then used to solve equation (4) for TW. The combined weight of solvent plus solute W is repeatedly read out from the balance on which the container rests in which the solution is being made as solvent is added to the solute within the container, and the flow of solvent is continued until a combined weight of solute plus solvent within the container equals the calculated weight TW.

BRIEF DESCRIPTION OF THE DRAWINGS

FIGS. 4A–4H are subroutines of the main program of FIG. 3; and

DESCRIPTION OF THE PREFERRED EMBODIMENTS

Figure 1:
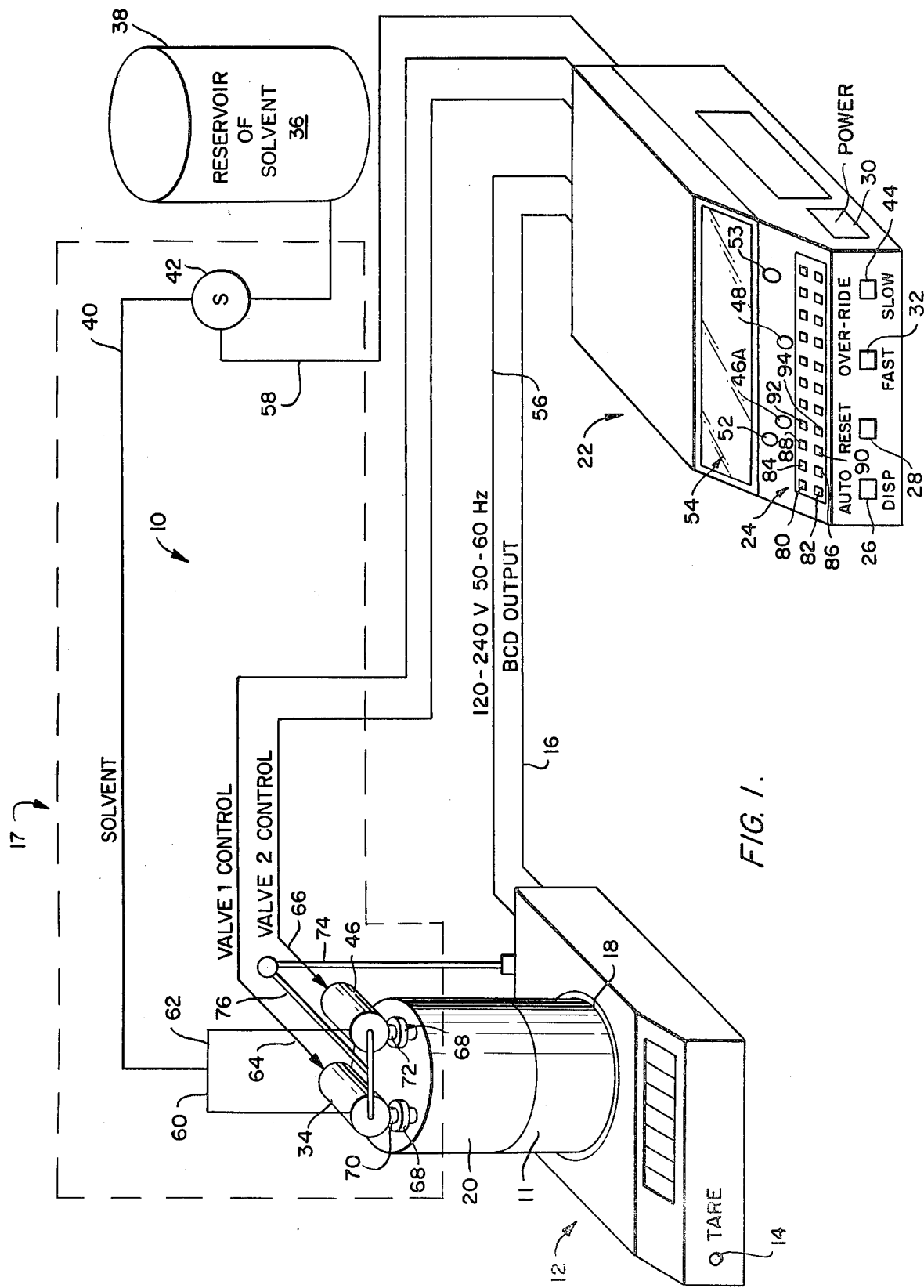
FIG. 1 is a schematic of the preferred form of apparatus to be used to mix the different types of solutions which may be mixed by the invention.

The invention is an apparatus for making solutions of specified molarity, normality, molality or weight percentage, corrected for water of hydration in which the volume of the solution prior to mixing may be either unknown or specified by the operator. When the volume is specified the actual volume obtained is dependent on the weight of solute in the container just prior to the addition of the solvent. The volume specification is used to alert the operator when the proper amount of solute has been added to meet the requirements for the amount of solution desired. The preferred form of the invention is controlled by a programmed microprocessor which permits the selective mixing of the foregoing eight modes of solution preparation.

The combined weight of solute and solvent TW necessary for making the specified type of solution from a solute weight WS is calculated in accordance with the following equations:

$$TW = (1000)\left(\frac{WS}{FW \times M}\right)[[1 + (K \times M)](SG)] \quad (1)$$

where TW is the combined weight of the solvent plus solute necessary to make the desired molar solution, K equals the specific gravity of a one molar solution of the solute −1 at a specified temperature which is stored in memory, SG is a scaling factor which corrects for the variation in the specific gravity as a junction of temperature, WS equals the measured weight of the solute that is to be mixed with the solvent to make the desired solution, FW equals the gram molecular weight of the compound which is stored in memory and M is the specified molarity which has been stored in memory by the operator prior to mixing. In accordance with the invention, the scaling factor SG may be omitted from the equation for calculating TW for molar solutions if the quantity K is based on data measured at a temperature close to the actual temperature of mixing of the desired molar solution or if maximum mixing accuracy is not required.

Normal Solutions Without Specified Volume $$TW = (1000)\left[\frac{WS}{\left(\frac{FW}{v}\right) \times N}\right]\left[\left[1 + \left(\frac{K}{v} \times N\right)\right](SG)\right] \quad (2)$$

where TW is the combined weight of solvent plus solute necessary to a make desired normal solution, K equals the specific gravity of a one molar solution of the solute at a specified temperature which is stored in memory, SG is a scaling factor which corrects for the variation in specific gravity of a one molar solution of compound which corrects for the variation of the specific gravity as a function of temperature, WS equals the measured weight of the solute that is to be mixed with the solvent to make the desired solution, N equals the specified normality which is entered into memory by the operator prior to mixing and v equals the valence of the solute which is stored in memory. In accordance with the invention, the scaling factor SG may be omitted from the equation for calculating TW for normal solutions if the quantity K is based on data measured at a temperature close to the actual temperature of mixing of the desired normal solution or if maximum accuracy is not required.

$$TW = \left[\frac{WS\left[1 - \frac{18.02 \times n}{FW}\right]}{[FW - (18.02 \times n)] \times m}\right][[[FW - (18.02 \times n)] \times m] + 1000] \quad (3)$$

where TW equals the combined weight of solvent and solute necessary to make a molal solution of specified concentration, WS equals the measured weight of solute that is to be mixed with the solvent to make the desired solution, FW equals the gram molecular weight of the compound stored in memory, n equals the number of water molecules associated with each molecule of compound within its crystalline structure which has been previously stored in memory or entered into memory by the operator, and m equals the specified molality of the solution which has been entered into memory by the operator prior to mixing. If the solute is anhydrous and n=0, the terms involving the parameter n may be ignored.

Percentage Weight Solutions Corrected For Water of Hydration Without Specified Volume $$TW = \frac{(WS)\left[1 - \frac{(18.02 \times n)}{FW}\right](100)}{\%} \quad (4)$$

where WS is the measured weight of solute that is to be mixed with the solvent to make the desired solution, FW equals the gram molecular weight of the compound stored in memory and n equals the number of molecules of water which are associated with each molecule of the compound in its crystallized state which has been previously stored in memory or entered into memory by the operator and the % is the desired weight dilution factor whih has been entered into memory by the operator.

Molar Solutions of Specified Volume $$TW = (V)[1 + (K \times M)] \quad (5)$$

where V is the specified volume and K and M have been defined supra in equation 1. The calculated weight TW obtained from equation 5 is substituted into a transformation of equation 1 (equation 1a supra) to calculate the solute weight WS necessary for mixing the desired concentration of molar solution of specified volume. The calculated solute weight WS is used only as a benchmark weight of the solute that should be added to the container to make the desired solution of the specified volume. The operator is alerted by audible and visual signals when the calculated weight of solute WS has been added. The actual weight of solute WS that was added to the container by the operator is then used to solve equation (1) for a TW and this value is used by the computer control system to control the addition of solvent to the container until the combined weight of solvent plus solute W equals TW.

Normal Solutions of Specified Volume $$TW = (V)\left[1 + \left(\frac{K}{v} \times N\right)\right] \quad (6)$$

where V is the estimated specified volume and K, v and N have been defined supra in equation 2. The calculated weight TW obtained from equation 6 is substituted into a transformation of equation 2 (equation 2a supra) to calculate the solute weight WS necessary for mixing the concentration of desired normal solution of specified volume. The calculated solute weight WS is used as a benchmark weight of the solute that should be added to the container to make the desired solution of the specified volume. The operator is alerted by audible and visual signals when the calculated weight of solute WS has been added. The actual weight of solute WS that was added to the container by the operator is then used to solve equation 2 for a TW and this value is used by the computer control system to control the addition of solvent to the container until the combined weight of solvent plus solute W equals TW.

Molal Solutions of Specified Volume $$TW = (V)[1 + (K \times M)] \qquad (7)$$

where V is the specified volume and K and M have been defined supra in equation 3. The calculated weight TW obtained from equation 7 is substituted into a transformation of equation 3 (equation 3a supra) to calculate the solute weight WS necessary for mixing the desired molal solution of specified volume. The calculated solute weight WS is used as a benchmark weight of the solute that should be added to the container to make the desired solution of the specified volume. The operator is alerted by audible and visual signals when the calculated weight of solute WS has been added. The actual weight of solvent WS that was added to the container by the operator is used to solve equation 3 for a TW and this value is used by the computer control system to control the addition of solvent to the container until the combined weight of solvent plus solute W equals TW.

Weight Percentage Solutions Corrected For Water of Hydration of Specified Volume $$TW = [V]\left[1 + \frac{(K \times \% \times 10)}{(FW - (18.02 \times n))}\right] \qquad (8)$$

where V is the specified volume and K, %, FW and n have been defined supra in equation 4. The calculated weight TW obtained from equation 8 is substituted into a transformation of equation 4 (equation 4(a) supra) to calculate the solute weight WS necessary for mixing the desired percent composition solution of specified volume. The calculated solute weight WS is used as a benchmark weight of the solute that should be added to the container to make the desired solution of the specified volume. The operator is alerted by audible and visual signals when the calculated weight of solute WS has been added. The actual weight of solute WS that was added to the container by the operator is used to solve equation 4 for a TW and this value is used by the computer control system to control the addition of solvent to the container until the combined weight of solvent plus solute W equals TW.

FIG. 1 illustrates a general schematic of the preferred form of apparatus which may be used to mix the eight types of solutions described above. The apparatus includes a controller 22 which includes an input/output device 24 for specifying inter alia the concentration and type of solution to be mixed, a balance 12 with TARE capability and apparatus 17 for controlling the flow of solvent 36 between a source of solvent 38 and a container 20 which contains the solute 11 to be mixed into the specified solution. The apparatus for controlling the flow of solvent 17 includes pump 42, conduit 40, first valve 34 and second valve 46. The flow of solvent 36 into the container 20 is under the control of the apparatus for controlling 17 when any one of the specified eight types of possible solutions are being mixed. The flow of solvent continues into a container 20 until the combined weight of solvent plus solute W, which is repeatedly read out by balance 12, is equal to the calculated weight TW for the specified type of solution. The balance 12 has a TARE control 14 and an output line 16 on which is repeatedly produced a signal of the weight placed on the pan 18 in binary coded decimal (BCD) format. As is known, the activation of the TARE control 14 produces a zero weight BCD output signal on line 16 while the container 20 is resting on the balance. The TARE control 14 is activated in the present invention when the pan 18 has a container 20 resting on it prior to placement of the solute 11 within the container which is to be mixed into a solution of specified concentration and type. The activation of the TARE control 14 prepares the balance for the measurement of the solute weight WS which is necessary to calculate TW for any of the desired types of solutions. Balances are commercially available with TARE controls which produce a BCD output which may be used in the present invention. A suitable commercially available balance having TARE capability and a BCD output is a model PC4000 which is manufactured by the Instrument Corporation of Hightstown, N.J. The controller 22 of the present invention includes a plurality of controls which include an input/output device 24 which is used by the operator for specifying the concentration and type of solution to be mixed in the manner described in detail infra in the flow charts of FIGS. 3 and 4A–4H, an automatic dispenser switch 26, a manual reset switch 28, an "on"-"off" power switch 30, a rapid manual dispense switch 32 is used to manually open a first rapid dispense valve 34 to the flow of solvent 36 from reservoir 38 through conduit 40, under the power of pump 42, a slow dispense switch 44 which is used to manually open a second valve 46 to the flow of solvent 36 from reservoir 38 through conduit 40 under the power of pump 42, a ready light 46A, an excessive volume light 48, a power on indicator light 52, maximum volume control 53 and display 54 which is used to convey messages from the computer control program to the user. The maximum volume control 53 specifies the maximum volume of solute plus solute which is permissible for mixing the solution into the concentration and type specified by the input/output device. The rapid manual dispense switch 32 and the slow manual dispense switch 44 may be used to manually override the automatic control of valves 34 and 46 by the controller 22 to permit selective flow control of solvent into container 20. The first valve 34 has a rated flow rate for a given pressure which is 10 times greater than the flow rate of the second valve 46. A power line 56 provides suitable electrical power for the balance 12 from the controller 22. A pump activation line 58 controls the activation of pump 42 for pumping solvent 36 from reservoir 38 through conduit 40, through either the first valve 34 or the second valve 46 into a container 20 in a manner to be hereinafter described. The power line for the controller 22 has been omitted. The conduit 40 contains a T section having an input which is coupled to the pump 42 and first and second outputs 60 and 62 which are respectively connected to the first and second valves 34 and 46. Valve control line 64 is connected between the controller 22 and the first valve 34 for selectively controlling the flow of solvent 36 from the pump 42 through the first valve at a higher rate in a manner to be hereinafter explained infra. Valve control line 66 is connected between the controller 22 and the second valve 46 for selectively controlling the flow of solvent 36 from the pump 42 through the second valve 46 in a manner to be hereinafter explained. The valves 34 and 46 have solenoids which are activated under the control of activation signals from the controller 22 over control lines 64 and 66. Valves 34 and 46 may be model V5 valves sold by Skinner Precision Industries, Inc. of New Britain, Conn. Bacterial filters 68 may be coupled between the outputs 70 and 72 of the first and second valves 34 and 46 to filter the solvent 36 prior to discharge into container 20. The valves 34 and 46 are supported above container 20 by the metallic stanchion 74 and a horizontal member 76. A plurality of keys 80, 82, 84, 86, 88, 90, 92 and 94 are dedicated to chosing the types of solutions which may be mixed with the invention in a manner described infra.

Figure 2:
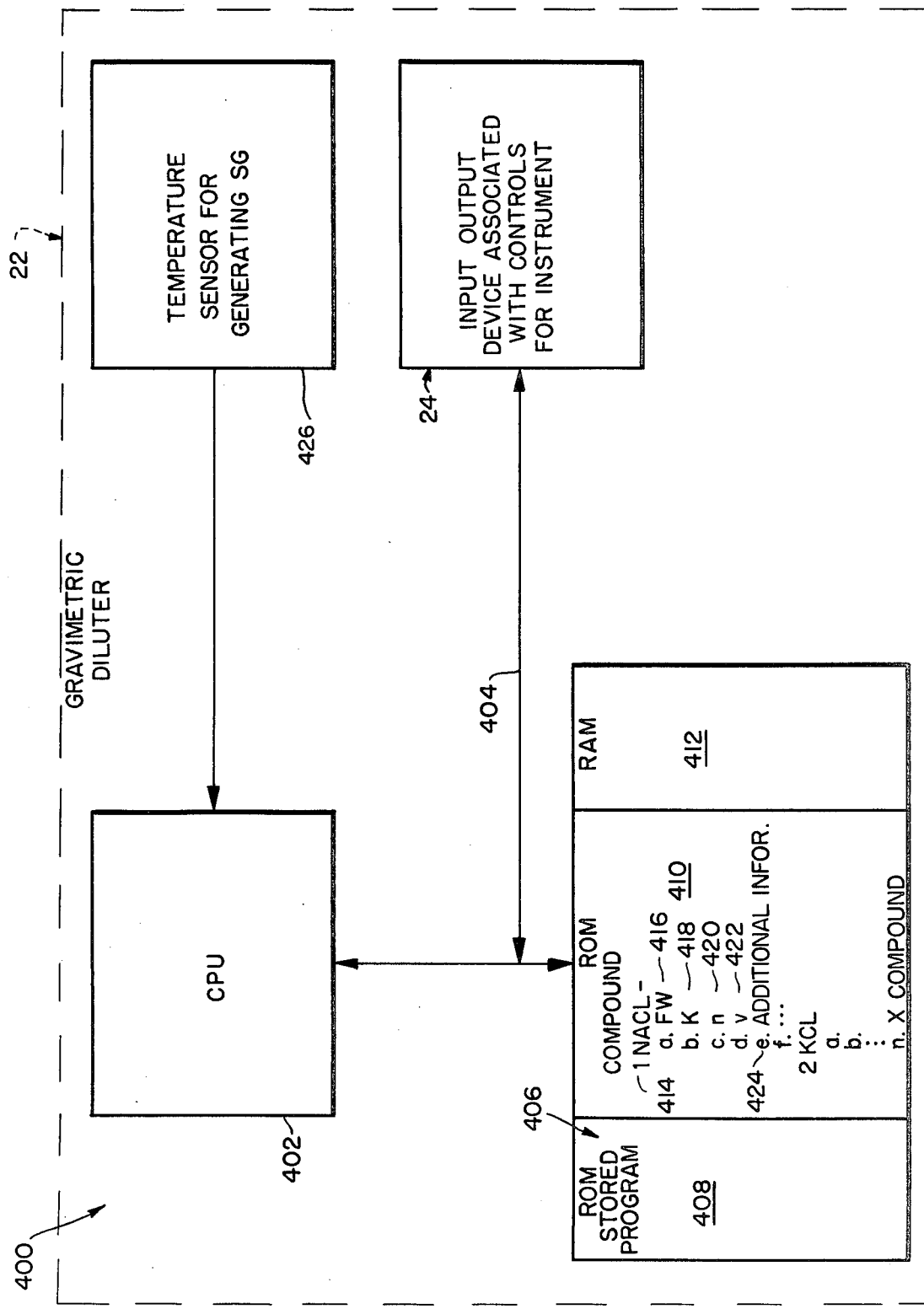
FIG. 2 is schematic of the computer system which controls the apparatus of FIG. 1 during the mixing of solutions.

FIG. 2 schematically illustrates the preferred form of computer control 400 of the present invention which is utilized by the microprocessor disposed within the controller 22. The preferred form of control is not limited to the use of a microprocessor since other types of computer control could be used to implement the invention but a microprocessor is preferred because of size and cost considerations. The input/output device 24 of the controller 22 is coupled to the central processing unit 402 via bus 404. The central processing unit 402 is coupled to a memory 406 via bus 404. The memory preferably includes two sections of ROM (read only memory) 408 and 410 and a single section of RAM (random access memory) 412. The section 408 stores the control program for the microprocessor which is described infra in the flow charts of FIGS. 3 and 4A–4H. Section 410 stores information required to calculate TW for compounds which the system is designed to have the capability of mixing solutions of selected type with or without a specified volume. Memory section 410 is organized by compounds. The actual number of compounds is only limited by the size of memory section 410. Each compound is stored with at least six items of information which are used in solving for TW in accordance with equations 1–8 supra to calculate the combined weight of solute and solvent necessary to mix the specified type of solution. The information required to calculate TW for molar, molal, normal and percentage compositions corrected for water of hydration includes the compound identification 414 such as compound one which is sodium chloride (NaCl), the gram molecular weight (FW) 416 of the compound, the specific gravity (K) 418 of a one molar solution of the compound at a specified temperature $-1$, the number of water molecules associated with each molecule of solute in the crystalline state of the compound 420 (n), the valence of the solute 422 (v), and other pertinent data 424. It should be understood that other uses of the memory space 424 may be implemented. The RAM section 412 of memory may be used to store volatile information such as the calculated weight TW, the specified type and concentration of the solution and other information which is read into memory from the input/output device 24 such as the maximum volume limit, the specified type and concentration of solution, etc. The temperature sensor 426 for generating the concentration factor SG is a thermistor which has a negative coefficient of resistance which approximates the decrease in the density of one mole solutions of the solute from the value used in calculating K in equations 1 and 2 supra. The scaling factor SG may be omitted if maximum accuracy is not required or if the temperature at which the selected solution is mixed is close to the temperature on which K is based.

Figure 3:
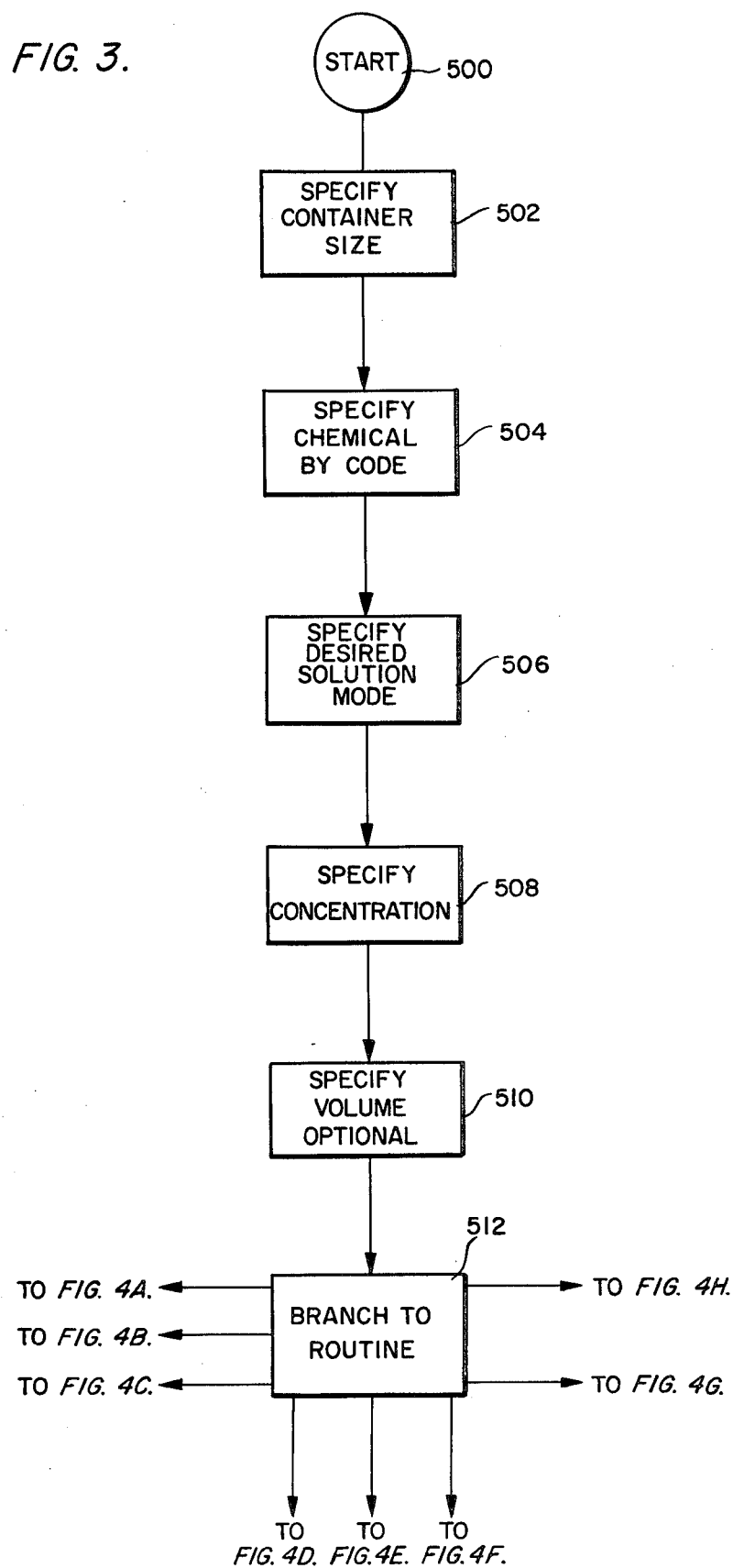
FIG. 3 is a flow chart of the main control program which is implemented by the computer system of FIG. 2.
Figure 4H:
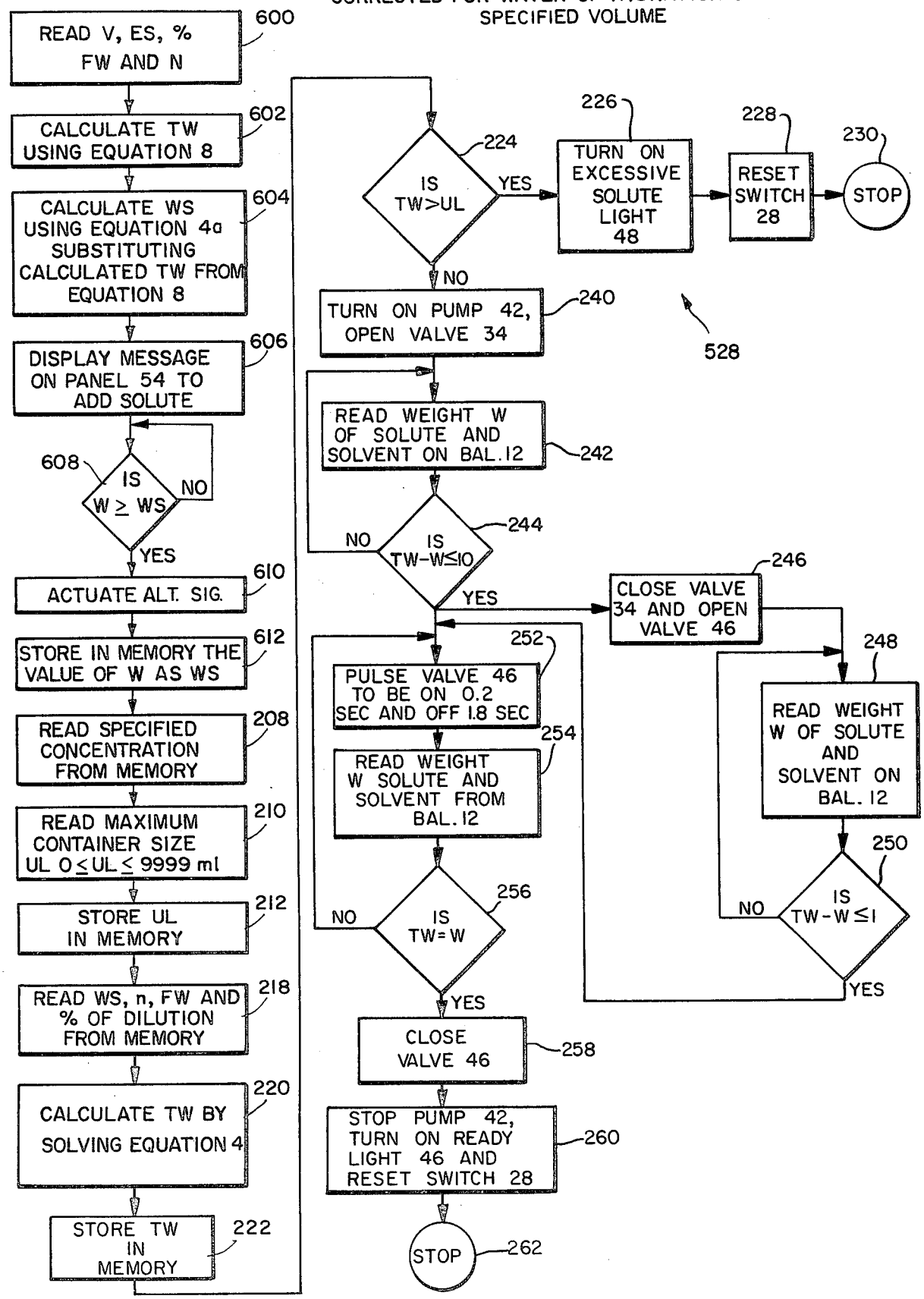

The microprocessor program for controlling the operation of the present invention is illustrated in FIGS. 3 and 4A–4H. The main program, which has the steps common to the mixing of all types of solutions, is illustrated in FIG. 3. The respective sub-routines for calculating TW for molar, normal, molal, and weight percentage solutions corrected for water of hydration when a desired final volume of the solution is not specified are illustrated respectively in FIGS. 4A–4D and the respective subroutines for calculating TW for molar, normal, molal and weight percentage solutions corrected for water of hydration when a desired volume of solution is specified are illustrated in FIGS. 4E–4H.

The main program is described with reference to FIG. 3 as follows. The main program is initiated by a start command 500 which is performed by the pressing of a start key in the input/output device 24 of the controller 22. The program then proceeds to block 502 where a display is placed on the input/output device 24 requesting the input into the RAM memory 412 of the identification of the rated container size in milliliters. The input of the container size into the RAM 412 is accomplished by an entry from the input/output device 24 keyboard. The program next proceeds to block 504 where the input of the identification of the chemical is specified by a code entered through the keyboard. The input required to choose a mixture of sodium chloride would be the number 1 because of the storage of information on sodium chloride in the number one space of ROM section 410. After the input of the solute identification, the program proceeds to block 506 where a display is placed on the input/output device 24 requesting the input of the type of solution requested, i.e., molar, normal, molal, or weight percentage corrected for water of hydration with or without a specified volume. The designation of the type of solution to be mixed is made by depressing one of eight dedicated keys, 80–94, on the keyboard of the input/output device 24. The designation of the type of solution is stored in the RAM memory section 412. The program then proceeds to block 508 where a display is made on the input/output device 24 which requests the designation of the concentration of the desired type of solution. The input of the concentration into the RAM memory section 412 is accomplished by entering the numerical designation of the type of solution, e.g, 1.5 for 1.5 molar, 0.75 for 0.75 normal, 2.0 for molal or 10 for %, etc. The program then proceeds to block 510 where the volume of the final solution is specified if a solution of a specified volume is to be mixed. The program then proceeds to block 512 where the program jumps to the subroutine for mixing the type of solution which was requested at block 506.

FIGS. 4A–4D respectively illustrate the subroutines 514, 516, 518 and 520 for calculating TW for molar, normal, molal and weight percentage solutions corrected for water of hydration where a final volume solution is not specified. Each of the routines 514, 516, 518 and 520 are identical except that the equation solved for determining TW for the designated type of solution differs and that different quantities are manipulated in solving the equations. FIGS. 4A–4D use identical reference numerals to identify identical steps and will be discussed conjunctively. The program proceeds from branch point 512 (FIG. 3) to the appropriate routine 514, 516, 518 and 520 for calculating the TW of the type of solution which has been requested. It is assumed that the following sequence of events has occurred in conjunction with the apparatus of FIG. 1 at the time of entry into the subroutine for calculating the TW of a designated type of solution: maximum volume UL of solute and solvent have been entered; the power has been turned on; a container 20 has been placed on the pan 18; the TARE control 14 has been depressed to cause the balance 12 to read out a weight in BCD format which is zero when the empty container 20 has been placed on the pan; a solute 11 to be mixed into the specified type and concentration of solution has been placed in the container 20; and the automatic dispense switch 26 has been depressed. The subroutine program begins at block 204 where the weight WS of the solute to 0.1 g in BCD format is read from the balance 12. The program proceeds to block 206 where the weight WS is stored in the RAM memory 412. The program then proceeds to block 208 where the specified concentration is read from the RAM memory 412 for the type of solution being mixed. The program then proceeds to block 210 where the maximum container size UL in milliliters is read from memory. The range of the maximum container size is $0 < UL < 9999$ ml. or to the capacity of the balance. The program then proceeds to block 212 where the maximum container size UL is stored in the RAM memory 412. The program then proceeds to block 218 where the appropriate parameters are read from memory for solving the equation for TW for the specified type of solution. It should be noted that the parameters which are read from memory in block 218 in FIGS. 4A, 4B, 4C and 4D are those necessary to solve the equation for the type of solution being made. The program then proceeds to block 220 where the weight TW is calculated for the type of designated solution. The calculation of TW for the particular type of solution is made in accordance with the solving of equations 1, 2, 3 or 4 supra. The program then proceeds to block 222 where TW for the particular solution being mixed is stored in the RAM memory 412. The program then proceeds to the decision point 224 where a determination is made if the volume of the specified solution will be too large for the specified container size. The determination is made by assuming a specific gravity of one for the solution so that the size of the container, which was specified at block 502 of FIG. 3, may be used directly to determine if the container would be overfilled by checking if the calculated TW is greater than UL. If the answer is "yes", the program branches to block 226 where an overlimit light 48 in the controller 22 is turned on to indicate that the weight of the solute plus the solvent for achieving the specified concentration is greater than the specified maximum container volume. The program then proceeds to block 228 where the controller 22 subcomponents are reset by activation of the switch 28 to prepare the system for mixing another solution. The program then proceeds to stopping point 230 which terminates all activity in the program. If the answer is "no" at decision point 224, the program proceeds to block 240 where the pump 42 is turned on and the valve 34 is opened. At this point, the pump is pumping solvent 36 into the container at the high flow capacity permitted by valve 34. The program then proceeds to block 242 where the BCD output from balance 12 of the combined weight of solute and solvent W is read. The program then proceeds to decision point 244 where a determination is made if $TW - W \leq 10$. If the answer is "no", the program loops back to block 242 and to decision point 244 where the calculation is made if $TW - W \leq 10$. As long as $TW - W > 10$, valve number 34 continues to be open and the highest flow rate of solvent into the container 20 takes place. The program continues to loop until $TW - W \leq 10$ at which point the program branches to block 246 where valve 34 is closed and valve 46 is opened. At this point the flow rate into the container 20 has been reduced by a factor of 10 as a consequence of the low rated flow capacity of valve 46 in comparison with valve 34. The program then proceeds to block 248 where the weight W of solute plus solvent is read from the balance 12. The program then proceeds to decision point 250 where a determination is made if $TW - W \leq 1$. If the answer is "no", the program loops back to block 248. If the answer is "yes", the program proceeds to block 252 where the valve is pulsed to be on for 0.2 seconds and pulsed off for 1.8 seconds. The program proceeds to block 254 where the weight of the solute plus solvent is read from balance 12. The program then proceeds to decision point 256 where a determination is made if $TW = W$. If the answer is "no", the program loops back to block 252 where the valve 46 is again pulsed. The program continues to loop until $TW = W$ at which time the program proceeds to block 258 where valve 46 is closed and valve 34 is maintained in its previously closed state. At this point in time, the specified concentration has been achieved because the combined weight of solute plus solvent equals TW. The program then proceeds to block 260 where pump 42 is turned off, the ready light 46 in the controller 22 is lit and the RAM memory elements of the controller are reset. The program then proceeds to stopping point 262 where no further program action occurs.

The invention may also be used to mix the four previously described types of solutions where the final volume is approximately specified. These four types of solutions with a specified final volume are mixed by solving the one of the equations 5–8 associated with the desired type of solution for the quantity TW which is the gravimetric equivalent of the final volume. This value, along with other stored and specified values, is substituted in one of the equations 1–4 transformed for the solution of WS for the type of solution desired (equations 1a–4a). The calculated weight WS is used in the subroutines set forth in FIGS. 4E–4H for the specified type of solution to aid the operator in the addition of solute to the container until the calculated weight WS is equaled or exceeded at which point the audible and visual signals are activated. The actual weight of solute which has been added to the container is stored in memory as the quantity WS. At this juncture, the remainder of the mixing of the specified type of solution of an estimated volume is completed by the same program steps for that type of solution which has been discussed above with reference to FIGS. 4A–4E.

FIGS. 4E–4H illustrate the subroutines 522,524,526, and 528 respectively for mixing molar, normal, molal and weight percentage solutions corrected for water of hydration. Each of the subroutines of FIGS. 4E–4H are identical except that different equations are initially solved (equations 5–8 for TW and equations 1a–4a for WS) and that different quantities are manipulated in finally solving the equations 1–4. FIGS. 4E–4H use identical reference numerals to identify identical parts and will be discussed conjunctively. Each subroutine begins at block 600 where the appropriate parameters are read from memory which are necessary to solve the particular equation 5–8 for calculating the gravimetric equivalent of final volume TW for the type of solution which is being mixed. The program next proceeds to block 602 where TW for the particular equation solution is calculated by solving the appropriate equation 5–8. The program next proceeds to block 604 where WS is calculated by substituting the value calculated at block 602 along with the other necessary stored values into the requisite equation 1a–4a for the type of solution which has been requested. The program next proceeds to block 606 where a message is placed on the display 54 that the solute should be added to the container. The program next proceeds to decision point 608 where a determination is made whether $W \geq WS$. The program continues to loop at 608 until the weight of solute is equal to or greater than the calculated weight WS. When the calculated weight WS is equaled by the actual weight of solute in the container 20, the program proceeds to block 610 where the alerting signals are actuated. The program next proceeds to block 612 where the actual weight of solute W in the container is stored in memory as WS. The final volume of molar and normal solutions will be equal to the specified volume only if the actual weight of solute W added to the container is equal to the quantity WS calculated at block 604. Otherwise, the final volume of solution will be approximately equal to the specified volume and will be either greater than the specified volume where the weight of actual solute is greater than the calculated weight W or less than the specified volume where the weight of actual solute is less than the calculated weight. With molal and weight percentage solutions which are corrected for water of hydration, an additional inaccuracy in final volume may result from having to estimate the specific gravity by equation 3(a) or 4(a). The remainder of the subroutines in FIGS. 4E–4H are identical to the subroutines described supra in FIGS. 4A–4D for mixing the same type of solution and will not be described in view of their previous description in conjunction with FIGS. 4A–4D.

Figure 5:
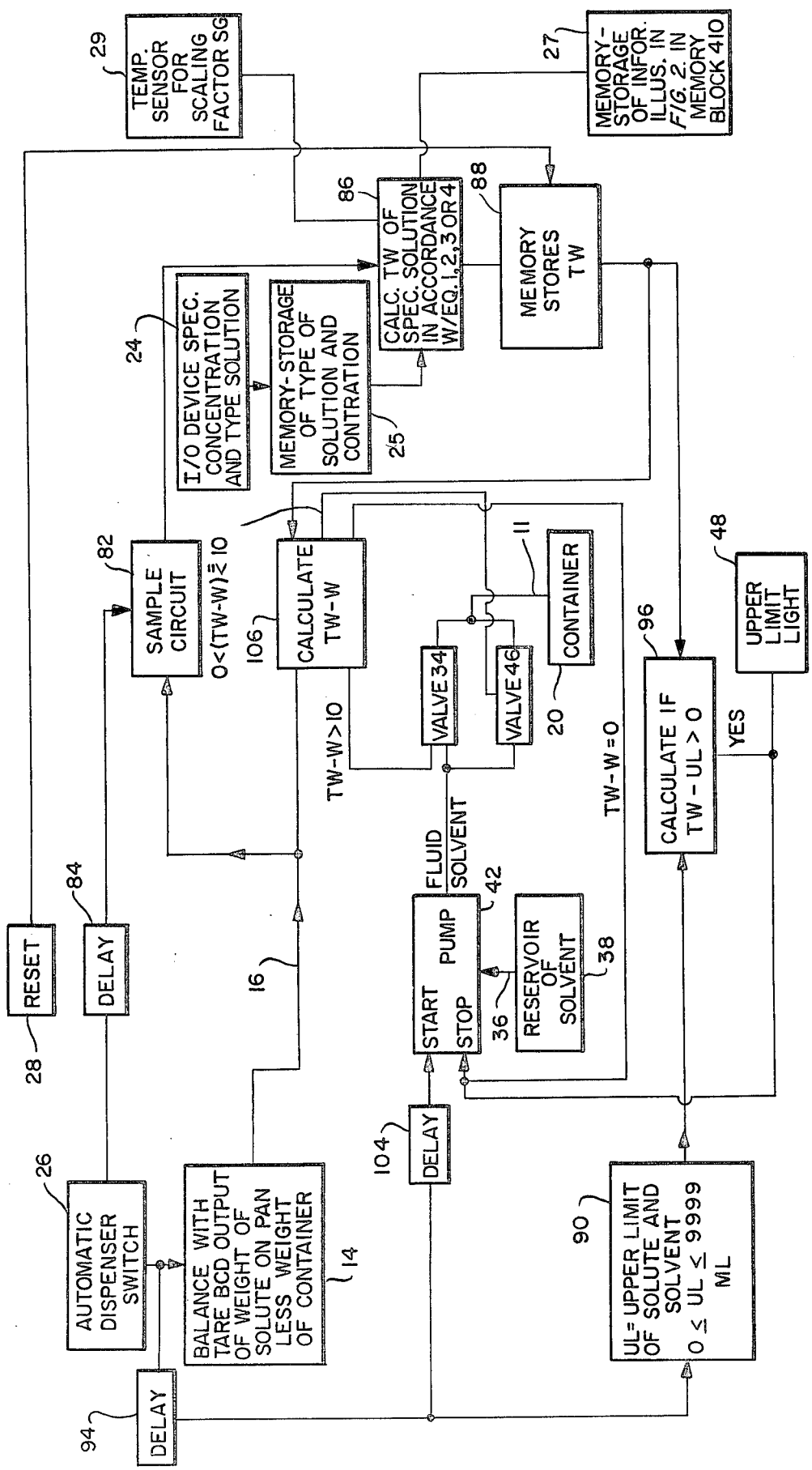
FIG. 5 is an electrical schematic of a control system for the apparatus of FIG. 1 which does not utilize a programmed digital computer.

FIG. 5 illustrates an electrical schematic of a control system for the apparatus of FIG. 1, which does not use a microprocessor control, that may be used for mixing molar, normal, molal and weight percentage solutions corrected for water of hydration which have an unspecified volume. The reference to TW in FIG. 5 should be understood to refer to the TW for the type of solution which is being mixed. While the embodiment of FIG. 5 uses digital storage and computation techniques, it should be understood that the invention may be implemented as an analog system. As described in conjunction with FIG. 1, the balance 12 produces a BCD output of the weight on the pan 18 on line 16. The TARE control 14 is activated after the container 20 is placed on the balance 12 but prior to the introduction of a solute 11 which is to be mixed to a predetermined concentration specified by the input/output device 24. The specified type of solution and concentration is stored in memory 25 to permit the calculation of TW when the weight of the solute WS is available after activation of the sample circuit 82. The automatic dispense switch 26, which is depressed after the TARE control 14 is activated and the solute 11 has been placed in the container 20, causes balance 12 to start to produce a BCD output of the weight of the solute plus solvent in the container 20 on line 16. The BCD output from balance 12 on line 16 is coupled to a sample circuit 82 of any conventional design that samples the BCD output of the weight of the solute 11 prior to the introduction of any solvent. The sample circuit 82 only couples the BCD output from the balance 12 to the means for calculating 86 when the signal from delay 84 is high. The time at which the BCD output is sampled by sample circuit 82 is controlled by the delay 84 which may be a one shot multivibrator or other suitable electrical delay, that produces a high level output signal for a short time interval after the automatic dispense switch is depressed. The time delay produced by the delay 84 need only be sufficient to permit the BCD weight output of the solute 11 to appear on line 82 after the depressing of the automatic dispense switch 26. The output of the sample circuit 82, is coupled to the means for calculating 86 which calculates TW in accordance with equations 1, 2, 3 or 4 depending upon the type of solution specified by the input/output device 24. A memory 27, which stores information identical to that contained in ROM section 410 illustrated in FIG. 2, is coupled to means for calculating TW 86. The memory provides the value of the constants and parameters needed to calculate the value of TW. A temperature sensor 29 for generating the scaling factor SG used in solving equations 1 and 2 supra is coupled to the means for calculating TW. The scaling factor SG may be generated by a thermistor which has a negative co-efficient of resistance which approximates the decrease in specific gravity of one molar solutions of solutes as a function of increasing temperature. Since the sample circuit 82 only couples the BCD weight of the solute 11 in the container 20 to be mixed to the means for calculating 86 for a short time interval after depressing the automatic dispense switch 26 during which the output from delay 84 sample circuit is high, the weight represented by the calculated weight TW is equal to the combined weight of the solute and solvent which will be present in the container 20 when the solute has been mixed to the concentration specified by the input/output device 24. The output TW from the means for calculating 86 is stored in a memory 88 of conventional design which is resettable by the manual reset switch 28. The depressing of the automatic dispense switch 26 also causes digital output signals to be produced from the maximum volume limit control 90 after a time delay produced by delay circuit 94 which may be a one shot multivibrator. The maximum volume limit, UL of solute plus solvent, is set before depressing of the automatic dispense switch 26. In the preferred embodiment, the maximum volume limit may vary between $0 < UL < 9999$ milliliters. It should be understood that the assumption is made that the maximum container volume in ml. is equal in grams to the maximum weight. The delay produced by delay 94 is longer than that produced by delay 84 in order to insure that the calculated weight TW has been calculated and stored prior to the output of the maximum volume determination circuit 90. The output from the maximum volume determination circuit 90 is coupled to a means for calculating 96 if $TW - UL > 0$. The output from the means for calculating 96 is coupled to the stop input of the pump 42 which immediately disables the pump if the calculated weight TW is greater off the valve for 1.8 seconds. The pulsating control signal is repeatedly applied to valve until $TW - W = 0$. The purpose of pulsating the valve 46 "on" and "off" when $0\ TW - W \leq 1$ is to permit the inherent lag in the production of the BCD output signal from the balance 12 on line 16 to not be a factor in shutting off the flow of solvent when $TW - W = 0$. Otherwise overshoot in the amount of solvent added to the solute could occur. When $TW - W$ equals zero, the means for calculating 106 produces an output signal which closes the second valve 46 to prevent further solvent flow through the second valve into the container 20 and shuts off the pump 42. At this instant in time, the mixing of the solution has been completed to a specified concentration.

EXAMPLE 1

A 0.1 Molar sucrose solution of unspecified volume is desired where WS=15.2 grams, M=0.1, K=0.1328 and FW equals 342.3 grams. The total weight of water plus sucrose TW is calculated by the controller 22 to be 449.1 grams by solving equation 1 supra. The 15.2 grams of sucrose is placed in the container 20 by the operator after the TARE control 14 on the balance 12 is activated but before the calculation for TW is made. The water is pumped into the container 20 under the control of controller 22 until the combined weight of water plus sucrose W is equal to the calculated weight TW of 449.1 grams at which point the flow of water into the container is stopped, resulting, when all solute is dissolved, in 449.1 grams of a 0.1 molar sucrose solution.

EXAMPLE 2

A 0.35 Normal solution $Na_2CO_3$ of unspecified volume is desired using $Na_2CO_3.10H_2O$ as the solute where WS=90.6 grams, n=0.35, k=0.1016, FW=286.16 grams and v=2. The total weight of water plus $Na_2CO_3.10H_2O$ TW is calculated by the controller 22 to be 1841.3 grams by solving equation 2 supra. The 90.6 grams of $Na_2CO_3.10H_2O$ is placed in container 20 by the operator after the TARE control 14 on the balance 12 is activated but before the TW calculation of TW is made. The water is pumped into the container 20 under the control of the controller 22 until the combined weight of water plus $Na_2CO_3.10H_2O$ is equal to TW at which point the flow of water into the container is stopped, resulting in 1841.3 grams of 0.35N $Na_2CO_3$ after all of the solute is dissolved.

EXAMPLE 3

A 1.5 molal solution of NaCl of unspecified volume is desired where WS=7.2 grams, m=1.5, FW=58.45 grams and n=0. The total weight of NaCl plus water TW is calculated by the controller to be 89.3 grams by solving equation 3 supra. The 7.2 grams of solute is placed in container 20 after TARE control 14 on the balance 12 has been activated but before the calculation for total weight of solute plus solvent TW is made. The water is pumped into the container 20 under the control of the controller 22 until the combined weight of NaCl plus water W is equal to TW at which point the flow of water into container 20 is stopped, thus resulting in 89.3 grams of a 1.5 molal solution of NaCl as soon as all of the solute is dissolved.

EXAMPLE 4

A 12% $Na_2CO_3$ solution using $Na_2CO_3.10H_2O$ of unspecified volume is desired where WS=9.8 grams, FW=286.10, n=10 and %=12. The total weight of $Na_2CO_3.10H_2O$ plus water TW is calculated by the controller 22 to be 30.2 grams by solving equation 4 supra. The 9.8 grams of solute is placed in the container 20 by the operator after TARE control 14 on balance 12 has been activated but before the calculation for total weight of solute plus solvent TW is made. The water is pumped into the container from the reservoir until the combined weight of water plus solute is equal to the calculated weight TW of 30.2 grams at which point the flow of water into the container is stopped and on dissolution of all solute, result in 30.2 grams of a 12% $Na_2CO_3$ solution.

EXAMPLE 5

A volume of about 2500 ml of a 0.1 molar sucrose solution is desired where M=0.1, K=0.1328, and FW=342.3. The gravimetric equivalent of 2500 ml is determined by solving equation 5 supra and found to be 2533.2 g. This value TW is substituted along with other values to solve equation 1a supra for WS which is 87.9 g. After activating TARE control 14 on balance 12, the operator adds sucrose until he is alerted by audible and visual signals when 87.9 grams of solute have been placed in container 20. The operator actually placed 88.0 g of sucrose in container 20. On pressing of automatic dispense switch 26, the total weight of solute plus solvent TW is calculated to be 2605.0 g by solving equation 1 supra. Water is pumped into container 20 under the control of controller 22 until the combined weight of solute plus solvent is 2605.0 grams at which point the flow of solvent is stopped, thus resulting in dissolution of the solute, in 2605 grams or about 2570 ml of a 0.1 Molar solution of sucrose.

EXAMPLE 6

A volume of 650 ml of a 2.1 Normal $Na_2CO_3$ is described made from $Na_2CO_3.10H_2O$ where FW=286.16, n=10, N=2.1, v=2, and K=0.1016. The gravimetric equivalent of 650 ml is determined by solving equation 6 supra to be 719.3 grams which is substituted as TW along with the other necessary values to solve equation 2a supra for WS which is 195.3 grams. After activating the TARE control 14 on balance 12, the operator adds $Na_2CO_3.10H_2O$ to container 20. When 195.3 grams have been added, the operator is alerted by audible and visual signals. The operator, in fact, placed 196.2 g $Na_2CO_3$ in container 20. On pressing the automatic dispense switch 26, the total weight of solute plus solvent TW was calculated to be 722.6 grams at which point the flow of solvent stops. Upon dissolution of the solute in the solvent, there is 722.6 grams, or about 652 ml of 2.1N $Na_2CO_3$ solution in container 20.

EXAMPLE 7

A volume of 425 ml of a 0.5 molal solution of $Na_2CO_3$ is desired to be made from $Na_2CO_3.10H_2O$ where FW=286.16, n=10, m=0.5, K=0.1016. The gravimetric equivalent of 425 ml is estimated by solving equation 7 supra to be 446.46 g, and this value for TW with the other necessary values are substituted in equation 3 supra to solve for WS which is 60.7 g after activating the TARE control 14 on balance 12, the operator adds $Na_2CO_3.10H_2O$ to container 20. When 60.7 g have been added, the operator is alerted by an audible and visual signal. The operator placed 60.7 grams of $Na_2CO_3.10H_2O$ in container 20. On pressing the automatic dispense switch 26, the total weight of the solute plus solvent TW is calculated to be 446.7 g by solving equation 3 supra. Water is pumped into container 20 under control of controller 22 until the combined weight of the solute plus solvent is 446.7 grams at which time the flow of solvent stops. At this point the container contains 446.7 g or about 425 ml of a 0.5 molal solution of $Na_2Co_3$ once all of the solute is dissolved.

EXAMPLE 8

A volume of 300 ml of a 12% $Na_2CO_3$ solution is desired to be made from $Na_2CO_3.10H_2O$ where FW=286.16, n=10, %=12 and K=0.1016. The gravimetric equivalent of 300 ml is estimated by solving equation 8 supra to be 334.5 g and this value of TW along with the other necessary values are substituted in equation 4a supra to solve for WS which is 108.4 g. After activating the TARE control 14 on balance 12, the operator adds $Na_2CO_3.10H_2O$ to container 20. When 108.4 g have been added, the operator is alerted by an audible and visual signal. The operator, in error, placed 110.1 grams of $Na_2CO_3.10H_2O$ in the container 20. On pressing the automatic dispense switch 26, the total weight of solute plus solvent TW is calculated to be 339.7 grams by solving equation 4 supra. Water is pumped into container 20 under the control of controller 22 until the combined weight of the solute plus solvent is 339.7 grams at which point the flow of solvent is stopped, thus resulting, on dissolution of the solute, in 339.7 grams or about 302 ml of a 12% solution of $Na_2CO_3$.

The term solvent as used in this application is not limited to water, although water is the most common solvent which is used for mixing molar, molal, normal or weight percentage solutions.

It is intended that the present invention not be limited in scope to the embodiments described above. Modifications may be made to the present invention without departing from its scope. It is intended that all such modifications fall within the scope of the appended claims.

We claim:

1. An apparatus for making a solution of specified molarity from a solute placed in a container by the addition of solvent to the container comprising:
   (a) means for repeatedly measuring the weight W of the solute plus any solvent within the container;
   (b) means for specifying the molarity M of the solution to be mixed from a solute within the container by the addition of solvent to the container;
   (c) fluid conducting means disposed between a source of solvent and the container for transferring solvent from the source to the container for mixing the solution of the specified molarity M within the container;
   (d) means for calculating TW wherein $$TW = (1000)\left(\frac{WS}{FW \times M}\right)[1 + (K \times M)]$$

WS equals the weight of the solute which is added to the container that is necessary to make the solution of specified molarity prior to mixing, K equals the specific gravity of a one molar solution of the solute measured at a particular temperature $-1$, and FW equals the gram molecular weight of the solute;
   (e) means for calculating TW $-$ W; and
   (f) means responsive to the means for calculating TW $-$ W for controlling the flow of solvent between the source and the container, the means for controlling causing the flow of solvent into the container to occur when TW $>$ W and to stop when TW $=$ W.

2. The apparatus of claim 1 wherein the quantity $[1+(K \times M)]$ is multiplied by a scaling factor SG wherein SG is a scaling factor which corrects for the variation in specific gravity of a one molar solution of the solute at any temperature at which the solution is mixed from the specific gravity of a one molar solution of the solute used in calculating K which is based upon measurement of specific gravity at a particular temperature.

3. An apparatus for making a solution of specified normality from a solute placed in a container by the addition of solvent to the container comprising:
   (a) means for repeatedly measuring the weight W of the solute plus any solvent within a container;
   (b) means for specifying the normality N of the solution to be mixed from a solute within the container by the addition of solvent to the container;
   (c) fluid conducting means disposed between a source of solvent and the container for transferring solvent from the source to the container for the purpose of mixing the solution of the specified normality within the container;
   (d) means for calculating TW wherein $$TW = (1000)\left[\frac{WS}{\left(\frac{FW}{v}\right) \times N}\right]\left[1 + \left(\frac{K}{v} \times N\right)\right]$$

k equals the specific gravity of a one molar solution of the solute at a particular temperature $-1$, WS equals the weight of the solute which is added to the container that is necessary to make the solution of specified normality, N equals the normality and v equals the valence of the solute;
   (e) means for calculating TW $-$ W; and
   (f) means responsive to the means for calculating TW $-$ W for controlling the flow of solvent between the source and the container, the means for controlling causing the flow of solvent into the container to occur when TW $>$ W and to stop when TW $=$ W.

4. The apparatus of claim 3 wherein the quantity $1+K/V \times N$ is multiplied by a scaling factor SG wherein SG is a scaling factor which corrects for the variation in specific gravity of a one molar solution of solute at any temperature at which the solution is mixed from the specific gravity of the solute used in calculating K which is based upon measurement of specific gravity at a particular temperature.

5. An apparatus for making a solution of specified molarity and approximate volume from a solute placed in a container by the addition of solvent to the container comprising:
   (a) means for repeatedly measuring the weight W of the solute plus any solvent within a container;
   (b) means for specifying the molarity M of the solution to be mixed within a container by the addition of solvent to the container;
   (c) means for specifying approximate volume V of the solution to be mixed;
   (d) means for calculating a gravimetric equivalent TW of the solution of volume V to be mixed wherein TW is calculated from the equation $$TW = (V)[1 + (K \times M)]$$

and is equal to the combined weight of solvent plus solute necessary to make the specified volume V of molar solution, and K equals the specific gravity of a one molar solution of the solute at a specified temperature $-1$ and M is the desired molarity;
   (e) fluid conducting means disposed between a source of solvent and the container for transferring solvent from the source to the container for mixing the solution;

(f) means for calculating WS from the equation $$WS = \frac{TW \times FW \times M}{1000[1 + (K \times M)]}$$

wherein WS equals the weight of the solute which is necessary to make the solution of specified molarity M and volume V, and FW equals the gram molecular weight of the solute;

(g) means for alerting an operator when the weight of solute which has been placed within the container is equal to or greater than the calculated weight WS;

(h) means for calculating TW in accordance with the equation $$TW = (1000)\left(\frac{WS}{FW \times M}\right)[1 + (K \times M)]$$

wherein WS is the weight of solute which has been added to the container that is less than, equals or exceeds the calculated WS;

(i) means for calculating TW−W; and (j) means responsive to the means for calculating TW−W for controlling the flow of solvent between the source and the container, the means for controlling causing the flow of solvent into the container to occur when TW>W and to stop when TW=W.

6. An apparatus for making a solution of specified normality and approximate volume from a solute placed in a container by the addition of solvent to the container comprising:

(a) means for repeatedly measuring the weight W of the solute plus any solvent within a container;

(b) means for specifying the normality N of the solution to be mixed within a container by the addition of solvent to the container which has the solute in it;

(c) means for specifying an approximate volume V of the solution to be mixed;

(d) means for calculating a gravimetric equivalent TW of the solution of volume V to be mixed wherein TW is calculated from the equation $$TW = V\left[1 + \left(\frac{K}{v} \times N\right)\right]$$

and is equal to the combined weight of solvent plus solute necessary to make the specified volume of normal solution wherein K equals the specific gravity of a one molar solution of the solute at a specified temperature −1, and v is the valence of the solute;

(e) fluid conducting means disposed between a source of solvent and the container for transferring solvent from the source to the container for mixing the solution;

(f) means for calculating WS from the equation $$WS = \frac{(TW) \times \left(\frac{FW}{v}\right)(N)}{1000\left[1 + \left(\frac{K}{v} \times N\right)\right]}$$

wherein WS equals the weight of the solute which is necessary to make the solution of specified normality N and volume V, and FW equals the gram molecular weight of the solute;

(g) means for alerting an operator when the weight of the solute which has been placed within the container is equal to or greater than the calculated weight WS;

(h) means for calculating TW in accordance with the equation $$TW = (1000)\left[\frac{WS}{\left(\frac{FW}{v}\right) \times N}\right]\left[1 + \left(\frac{K}{v} \times N\right)\right]$$

wherein WS is the weight of solute which has been added to the container that is less than, equals or exceeds the calculated WS:

(i) means for calculating TW−W; and (j) means responsive to the means for calculating TW−W for controlling the flow of solvent between the source and the container, the means for controlling causing the flow of solvent into the container to occur when TW>W and to stop when TW=W.

7. An apparatus for making a solution of specified molality and approximate volume from a solute placed in a container by the addition of solvent into the container comprising:

(a) means for repeatedly measuring the weight W of the solute plus any solvent with a container;

(b) means for specifying the molality m of the solution to be mixed within a container by the addition of solvent to the container;

(c) means for specifying an approximate volume V of the solution to be mixed;

(d) means for calculating a gravimetric equivalent TW of the solution of volume V to be mixed wherein TW is calculated from the equation $$TW = (V)[1 + K \times m]$$

and is equal to the combined weight of solvent plus solute necessary to make the specified volume V of molal solution, and K is the specific gravity of a one molar solution of the solute at a specified temperature −1;

(e) fluid conducting means disposed between a source of solvent and the container for transferring solvent from the source to the container for mixing the solution;

(f) means for calculating WS from the equation $$WS = \frac{TW\left[FW - \frac{(18.02 \times n)}{FW}\right](m)(FW)}{[[[FW - (18.02 \times n)] \times m] + 1000][FW - (18.02 \times n)]}$$

wherein WS equals the weight of the solute which is necessary to make the solution of specified molality m and volume V, FW equals the gram molecular weight of the solute and n equlas the number of water molecules associated with each molecule of solute within the crystalline structure of the solute;

(g) means for alerting an operator when the weight of the solute which has been placed within the container is equal to or greater than the calculated weight WS;

(h) means for calculating TW in accordance with the equation $$TW = \left[\frac{WS\left[1 - \frac{(18.02 \times n)}{FW}\right]}{[FW - (18.02 \times n) \times m}\right] [[[FW - (18.02 \times n)] \times m] + 1000]$$

wherein WS is a weight of solute which has been added to the container which is less than, equals or exceeds the calculated WS;

(i) means for calculating $TW - W$; and
(j) means responsive to the means for calculating $TW - W$ for controlling the flow of solvent between the source and the container, the means for controlling causing the flow of solvent into the container to occur when $TW > W$ and to stop when $TW = W$.

8. An apparatus for making a solution of specified weight percentage corrected for water of hydration and approximate volume from a solute placed in a container by the addition of solvent to the container comprising:

(a) means for repeatedly measuring the weight W of the solute plus any solvent within a container;
(b) means for specifying the % of the solution to be mixed within a container by the addition of solvent to the container which has the solute in it;
(c) means for specifying an approximate volume V of the solution to be mixed;
(d) means for calculating a gravimetric equivalent TW of the solution to be mixed wherein TW is calculated from the equation $$TW = \frac{V[1 + (K \times \% \times 10)]}{FW - (18.02 \times n)}$$

and is equal to the combined weight of solvent plus solute necessary to make the specified volume of % solution, n is the number of molecules of water combined in each molecule of solute, FW is the gram molecular weight of the solute and K equals the specific gravity of a one molar solution of the solute at specified temperature $-1$;

(e) fluid conducting means disposed between a source of solvent and the container for transferring solvent from the source to the container for mixing the solution;
(f) means for calculating WS from the equation $$WS = \frac{(TW)}{(100)} \frac{(\%) FW}{[FW - (18.02 \times n)]}$$

wherein WS equals the weight of the solute which is necessary to make the solution of specified % corrected for water of hydration and volume V;

(g) means for alerting an operator when the weight of the solute which has been placed within the container is equal to or greater than the calculated weight WS;

(h) means for calculating TW in accordance with the equation $$TW = \frac{(WS)\left[1 - \frac{(18.02 \times n)}{FW}\right](100)}{\% \text{ [dilution]}}$$

wherein WS is a weight of solute which has been added to the container which is less than, equals or exceeds the calculated WS;

(i) means for calculating $TW - W$; and
(j) means responsive to the means for calculating $TW - W$ for controlling the flow of solvent between the source and the container, the means for controlling causing the flow of solvent into the container to occur when $TW > W$ and to stop when $TW = W$.

9. A process for mixing solutions of specified molarity and approximate volume comprising:

(a) specifying a molarity M of a solution to be mixed in a container by the addition of a solvent to a solute within the container;
(b) specifying an approximate volume V of solution of the specified molarity M;
(c) calculating a weight of solvent plus solute TW for mixing the solution of specified approximate volume V;
(d) calculating a weight of solute WS required for mixing the solution with the weight TW of solute plus solvent;
(e) adding a weight of solute to the container which is less than, equal to or greater than WS;
(f) calculating a weight of solvent plus solute TW for mixing the solution of specified molarity M from the actual weight of solute WS which has been added to the container; and
(g) adding solvent to the container until the weight of solvent plus solute is equal to the calculated weight TW for mixing the solution of specified molarity M from the actual weight of solute WS which has been added to the container.

10. A process in accordance with claim 9 wherein:

(a) the calculation in step (c) of claim 9 is made in accordance with the equation $$TW = (V)[1 + (K \times M)]$$

wherein K equals the specific gravity of a one molar solution of the solute measured at a particular temperature $-1$;

(b) the calculation in step (d) of claim 9 is made in accordance with the equation $$WS = \frac{TW \times FW \times M}{1000 [1 + (K \times M)]}$$

wherein FW equals the gram molecular weight of the solute; and
(c) the calculation in step (f) of claim 9 is made in accordance with the equation $$TW = (1000)\left(\frac{WS}{FW \times M}\right)[1 + (K \times M)]$$

11. A process in accordance with claim 10 wherein the quantity $1+K\times M$ is multiplied by a scaling factor SG wherein SG is a scaling factor which corrects for the variation in specific gravity of a one molar solution of solute at any temperature at which the solution is mixed from the specific gravity of the solute used in calculating K which is based upon a measurement of specific gravity at a particular temperature.

12. A process for mixing solutions of specified normality and approximate volume comprising:
   (a) specifying a normality N of a solution to be mixed in a container by the addition of a solvent to a solute within the container;
   (b) specifying an approximate volume V of solution of the specified normality N;
   (c) calculating a weight of solvent plus solute TW for mixing the solution of specified approximate volume;
   (d) calculating a weight of solute WS required for mixing the solution with the weight TW of solute plus solvent;
   (e) adding solute to the container which is less than, equal to or greater than WS;
   (f) calculating a weight of solvent plus solute TW for mixing the solution of specified normality N from the actual weight of solute WS which has been added to the container; and
   (g) adding solvent to the container until the weight of solvent plus solute is equal to the calculated weight TW necessary to mix the solution of specified normality N from the actual weight of solute WS which has been added to the container.

13. A process in accordance with claim 12 wherein:
   (a) the calculation in step (c) of claim 12 is made in accordance with the equation $$TW = (V)\left[1 + \frac{K}{v} \times N\right)$$

where K equals the specific gravity of a one molar solution of the solute at a particular temperature $-1$, and v equals the valence of the solute which is stored in memory;
   (b) the calculation in step (d) of claim 12 is made in accordance with the equation $$WS = \frac{(TW)\left(\frac{FW}{v}\right)(N)}{(1000)\left[1 + \left(\frac{K}{v} \times N\right)\right]}$$

wherein FW equals the gram molecular weight of the solute and
   (c) the calculation in step (f) of claim 12 is made in accordance with the equation $$TW = (1000)\left[\frac{WS}{\left(\frac{FW}{v}\right) \times N}\right]\left[1 + \left(\frac{K}{v}\right) \times N\right]$$

14. A process in accordance with claim 13 wherein the quantity $1+K/v\times N$ is multiplied by a scaling factor SG where SG is a scaling factor which corrects for the variation in specific gravity of a one molar solution of solute at any temperature at which the solution is mixed from the specific gravity of the solute used in calculating K which is based upon a measurement of specific gravity at a particular temperature.

15. A process for mixing solutions of specified molality and approximate volume comprising:
   (a) specifying a molality m of a solution to be mixed in a container by the addition of a solvent to a solute within the container;
   (b) specifying an approximate volume V of solution of the specified molality m;
   (c) calculating a weight of solvent plus solute TW for mixing the solution of specified approximate volume;
   (d) calculating a weight of solute WS required for mixing the solution with the weight TW of solute plus solvent;
   (e) adding solute to the container which is less than, equal to or greater than WS;
   (f) calculating a weight of solvent plus solute TW for mixing the solution of specified molality m from the actual weight of solute WS which has been added to the container; and
   (g) adding solvent to the container until the combined weight of solvent plus solute is equal to the calculated weight TW necessary to mix the solution of specified molality m from the actual weight of solute WS which has been added to the container.

16. A process in accordance with claim 15 wherein:
   (a) the calculation in step (c) of claim 15 is made in accordance with the equation $$TW=(V)[1+(K\times m)]$$

wherein K equals the specific gravity of a one molar solution of the solute measured at a particular temperature $-1$;
   (b) the calculation in step (d) of claim 15 is made in accordance with the equation $$WS = \frac{(TW)[FW - (18.02 \times n)](m)(FW)}{[[[(FW - (18.02 \times n)] \times m] + 1000][FW - (18.02 \times n)]}$$

wherein FW equals the gram molecular weight of the solute and n is the valence of the solute; and
   (c) the calculation in step (f) of claim 15 is made in accordance with the equation $$TW = \left[\frac{\frac{WS[1 - 18.02 \times n]}{FW}}{[FW - (18.02 \times n)] \times m}\right][[[FW - (18.02 \times n)] \times m] + 1000]$$

17. A process for mixing solutions of specified weight percentage corrected for water of hydration and approximate volume comprising:
(a) specifying a weight % of a solution to be mixed in a container by the addition of a solvent to a solute within the container;
(b) specifying an approximate volume V of solution of the specified weight %;
(c) calculating a weight of solvent plus solute TW for mixing the solution of specified approximate volume;
(d) calculating a weight of solute WS required for mixing the solution with a weight TW of solute M plus solvent;
(e) adding solute to the container which is less than, equal to or greater than WS;
(f) calculating a weight of solvent plus solute TW for mixing the solution of specified weight % from the actual weight of solute WS which has been added to the container; and
(g) adding solvent to the container until the combined weight of solvent plus solute is equal to the calculated weight TW necessary to mix the solution of specified weight % from the actual weight of solute WS which has been added to the container.

18. A process in accordance with claim 17 wherein:
(a) the calculation in step (c) of claim 17 is made in accordance with the equation $$TW = [v]\left[1 + \frac{(K \times \% \times 10)}{(FW - (18.02 \times n))}\right]$$

wherein K equals the specific gravity of a one molar solution of the solute measured, FW equals the gram molecular weight at a particular temperature $-1$ of the solute, and n is the number of molecules of water combined in each molecule of the solute;
(b) the calculation in step (d) of claim 17 is made in accordance with the equation $$WS = \frac{(TW)(\%)(Fw)}{(100)[FW - (18.02 \times n)]}$$

and
(c) the calculation in step (f) of claim 17 is made in accordance with the equation $$TW = \frac{(WS)\left[1 - \frac{(18.02 \times n)}{FW}\right](100)}{\%}$$

19. An apparatus for making a solution of specified molarity from a solute placed in a container by the addition of solvent to the container comprising:
(a) means for repeatedly measuring the weight W of the solute plus any solvent within a container;
(b) means for specifying the molarity M of the solution to be mixed from a solute within the container by the addition of solvent to the container;
(c) fluid conducting means disposed between a source of solvent and the container for transferring solvent from the source to the container for mixing the solutions of the specified molarity M within the container;
(d) means for calculating TW wherein TW is the combined weight of solvent plus solute necessary to make the solution;
(e) means for calculating TW$-$W; and
(f) means responsive to the means for calculating TW$-$W for controlling the flow of solvent between the source and the container, the means for controlling causing the flow of solvent into the container to occur when TW$>$W and to stop when TW$=$W.

20. An apparatus for making a solution of specified normality from a solute placed in a container by the addition of solvent to the container comprising:
(a) means for repeatedly mesuring the weight W of the solute plus any solvent within a container;
(b) means for specifying the normality N of the solution to be mixed from a solute within the container by the addition of solvent to the container;
(c) fluid conducting means disposed between a source of solvent and the container for transferring solvent from the source to the container for the purpose of mixing the solution of the specified normality within the container;
(d) means for calculating TW wherein TW is the combined weight of solvent plus solute necessary to make the solution;
(e) means for calculating TW$-$W; and
(f) means responsive to the means for calculating TW$-$W for controlling the flow of solvent between the source and the container, the means for controlling causing the flow of solvent into the container to occur when TW$>$W and to stop when TW$=$W.

21. An apparatus for making a solution of specified molarity and approximate volume in accordance with claim 5 wherein the quantity $1+K\times M$ is multiplied by a scaling factor SG wherein SG is a scaling factor which corrects for the variation in specific gravity of a one molar solution of solute at any temperature at which the solution is mixed from the specific gravity of the solute used in calculating K which is based upon a measurement of specific gravity at a particular temperature.

22. An apparatus for making a solution of specified normality and approximate volume in accordance with claim 6 wherein the quantity $1+K/v\times N$ is multiplied by a scaling factor SG wherein SG is a scaling factor which corrects for the variation in specific gravity of a one molar solution of solute at any temperature at which the solution is mixed from the specific gravity of the solute used in calculating K which is based upon a measurement of specific gravity at a particular temperature.

* * * * *